United States Patent
Guo et al.

(10) Patent No.: US 8,455,604 B1
(45) Date of Patent: *Jun. 4, 2013

(54) POLYSILANE COMPOSITIONS, METHODS FOR THEIR SYNTHESIS AND FILMS FORMED THEREFROM

(75) Inventors: Wenzhuo Guo, Cupertino, CA (US); Vladimir K. Dioumaev, Mountain View, CA (US); Joerg Rockenberger, Redwood City, CA (US); Brent Ridley, San Carlos, CA (US)

(73) Assignee: Kovio, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/543,557

(22) Filed: Jul. 6, 2012

Related U.S. Application Data

(60) Continuation of application No. 12/343,200, filed on Dec. 23, 2008, now Pat. No. 8,236,916, which is a continuation of application No. 11/893,054, filed on Aug. 13, 2007, now Pat. No. 7,491,782, which is a division of application No. 11/246,014, filed on Oct. 6, 2005, now Pat. No. 7,485,691.

(60) Provisional application No. 60/617,562, filed on Oct. 8, 2004.

(51) Int. Cl.
  *C08G 77/00* (2006.01)
  *C07F 7/02* (2006.01)
  *C07F 7/21* (2006.01)

(52) U.S. Cl.
  USPC ............. 528/31; 528/33; 528/37; 528/43; 556/430

(58) Field of Classification Search
  None
  See application file for complete search history.

(56) References Cited

U.S. PATENT DOCUMENTS

| | | | |
|---|---|---|---|
| 4,052,430 A | 10/1977 | Yajima et al. | |
| 4,276,424 A | 6/1981 | Peterson, Jr. et al. | |
| 4,310,482 A | 1/1982 | Baney | |
| 4,358,576 A | 11/1982 | Yajima et al. | |

(Continued)

FOREIGN PATENT DOCUMENTS

| CN | 1297578 A | 5/2001 |
|---|---|---|
| CN | 1407018 A | 4/2003 |

(Continued)

OTHER PUBLICATIONS

Matsuki Yasuo; "Process for Formation of Silicon Oxide Films"; esp@cenet; Chinese Publication No. CN 1297578; Publication Date: May 30, 2001; esp@cenet Database—Worldwide, http://v3.espacenet.com/textdoc? DB=EPODOC&IDX=CN1297578&F=0.

(Continued)

*Primary Examiner* — Robert S Loewe
(74) *Attorney, Agent, or Firm* — Andrew Fortney

(57) ABSTRACT

Polysilanes, inks containing the same, and methods for their preparation are disclosed. The polysilane may have the formula H-[(AHR)$_n$(c-A$_m$H$_{pm-2}$)$_q$]—H, where A is independently Si or Ge; R is H, -A$_a$H$_{a+1}$R$_a$, halogen, aryl or substituted aryl; (n+a)≧10 if q=0, q≧3 if n=0, and (n+q)≧6 if both n and q≠0; p is 1 or 2; and m is from 3 to 12. The method may include combining a silane compound of the formula AH$_a$R$^1_{4-a}$, A$_k$H$_g$R$^1_h$ and/or c-A$_m$H$_{pm}$R$^1_{rm}$ with a catalyst of the formula R$^4_x$R$^5_y$MX$_z$ (or an immobilized derivative thereof) to form a poly(aryl)silane; then washing the poly(aryl)silane with an aqueous washing composition and contacting the poly(aryl)silane with an adsorbent to remove the metal M. Alternatively, the method may include halogenating a polyarylsilane and reducing the halopolysilane with a metal hydride to form the polysilane.

24 Claims, 8 Drawing Sheets

U.S. PATENT DOCUMENTS

| | | | |
|---|---|---|---|
| 4,537,942 | A | 8/1985 | Brown-Wensley et al. |
| 4,554,180 | A | 11/1985 | Hirooka |
| 4,611,035 | A | 9/1986 | Brown-Wensley et al. |
| 4,683,145 | A | 7/1987 | Nishimura et al. |
| 4,683,146 | A | 7/1987 | Hirai et al. |
| 4,704,444 | A | 11/1987 | Brown-Wensley et al. |
| 4,726,963 | A | 2/1988 | Ishihara et al. |
| 4,759,947 | A | 7/1988 | Ishihara et al. |
| 4,820,788 | A | 4/1989 | Zeigler |
| 4,822,703 | A | 4/1989 | Badesha et al. |
| 4,830,890 | A | 5/1989 | Kanai |
| 4,835,005 | A | 5/1989 | Hirooka et al. |
| 4,841,083 | A | 6/1989 | Nagai et al. |
| 4,992,520 | A | 2/1991 | Zeigler |
| 5,153,295 | A | 10/1992 | Whitmarsh et al. |
| 5,204,380 | A | 4/1993 | Seyferth et al. |
| 5,237,033 | A | 8/1993 | Tabei et al. |
| 5,358,987 | A | 10/1994 | Kanai et al. |
| 5,700,400 | A | 12/1997 | Ikai et al. |
| 5,798,428 | A | 8/1998 | Schwab et al. |
| 5,866,471 | A | 2/1999 | Beppu et al. |
| 5,942,637 | A | 8/1999 | Boudjouk et al. |
| 6,005,036 | A | 12/1999 | Carrozza et al. |
| 6,140,448 | A | 10/2000 | Choi et al. |
| 6,174,982 | B1 | 1/2001 | Nishida et al. |
| 6,503,570 | B2 | 1/2003 | Matsuki et al. |
| 6,514,801 | B1 | 2/2003 | Yudasaka et al. |
| 6,517,911 | B1 | 2/2003 | Matsuki |
| 6,518,087 | B1 | 2/2003 | Furusawa et al. |
| 6,527,847 | B1 | 3/2003 | Matsuki |
| 6,541,354 | B1 | 4/2003 | Shimoda et al. |
| 6,610,872 | B1 | 8/2003 | Choi et al. |
| 6,767,775 | B1 | 7/2004 | Yudasaka et al. |
| 6,884,700 | B2 | 4/2005 | Aoki et al. |
| 6,908,796 | B2 | 6/2005 | Furusawa |
| 7,067,069 | B2 | 6/2006 | Shiho et al. |
| 7,078,276 | B1 | 7/2006 | Zurcher et al. |
| 7,314,513 | B1 | 1/2008 | Zurcher et al. |
| 2001/0021760 | A1 | 9/2001 | Matsuki et al. |
| 2003/0045632 | A1 | 3/2003 | Shiho et al. |
| 2003/0087110 | A1 | 5/2003 | Furusawa et al. |
| 2003/0148024 | A1 | 8/2003 | Kodas et al. |
| 2003/0219934 | A1 | 11/2003 | Furusawa |
| 2003/0229190 | A1 | 12/2003 | Aoki et al. |
| 2004/0029364 | A1 | 2/2004 | Aoki et al. |
| 2004/0248429 | A1 | 12/2004 | Aoki |
| 2005/0145163 | A1 | 7/2005 | Matsuki et al. |
| 2005/0176183 | A1 | 8/2005 | Aoki |
| 2005/0181566 | A1 | 8/2005 | Machida et al. |
| 2006/0159859 | A1 | 7/2006 | Iwasawa |
| 2006/0185712 | A1 | 8/2006 | Shiho et al. |
| 2006/0198966 | A1 | 9/2006 | Kaino et al. |
| 2008/0085373 | A1 | 4/2008 | Karshtedt et al. |

FOREIGN PATENT DOCUMENTS

| | | | |
|---|---|---|---|
| DE | 3122992 | A1 | 2/1982 |
| EP | 1 085 560 | A1 | 3/2001 |
| EP | 1 085 579 | A1 | 3/2001 |
| EP | 1 087 428 | A1 | 3/2001 |
| EP | 1 087 433 | A1 | 3/2001 |
| EP | 1 113 502 | A1 | 7/2001 |
| EP | 0 902 030 | B1 | 10/2002 |
| EP | 1 284 306 | A2 | 2/2003 |
| EP | 1 357 154 | A1 | 10/2003 |
| GB | 2077710 | A | 12/1981 |
| JP | 57-27915 | A | 2/1982 |
| JP | 60-242612 | A | 12/1985 |
| JP | 61-200130 | A | 9/1986 |
| JP | 4-334551 | A | 11/1992 |
| JP | 5-230219 | A | 9/1993 |
| JP | 6-191821 | A | 7/1994 |
| JP | 7-267621 | A | 10/1995 |
| JP | 9-45922 | A | 2/1997 |
| JP | 9-237927 | A | 9/1997 |
| JP | 11-79727 | A | 3/1999 |
| JP | 11-171528 | A | 6/1999 |
| JP | 2000-7317 | A | 1/2000 |
| JP | 2000-31066 | A | 1/2000 |
| JP | 2002-203794 | A | 7/2002 |
| JP | 2002-246384 | A | 8/2002 |
| JP | 2003-55556 | A | 2/2003 |
| JP | 2003-92297 | A | 3/2003 |
| JP | 2003-124486 | A | 4/2003 |
| JP | 2003-313299 | A | 11/2003 |
| JP | 2003-318120 | A | 11/2003 |
| JP | 2004-311945 | A | 11/2004 |
| JP | 2005-219981 | A | 8/2005 |
| WO | 0059014 | A1 | 10/2000 |
| WO | 0059022 | A1 | 10/2000 |
| WO | 0059041 | A1 | 10/2000 |
| WO | 2004110929 | A1 | 12/2004 |

OTHER PUBLICATIONS

Shio Kooji and Katoo Nichika; "Silane Composition, Silicon Film Forming Method and Manufacture of Solar Cells"; esp@cenet; Chinese Publication No. CN1407018; Publication Date: Apr. 2, 2003; esp@cenet Database—Worldwide, http://v3.espacenet.com/textdoc?DB=EPODOC&IDX=CN1407018&F=0.

Phillip John, Michael John Tricker and Michael John Kingston Thomas; "Process for Preparing Polysilane"; esp@cenet; European Publication No. DE3122992; Publication Date: Feb. 4, 1982; esp@cenet Database—Worldwide, http://v3.espacenet.com/textdoc?DB=EPODOC&IDX=DE3122992&F=0.

Philip Raymond Boudjouk, Beon-Kyu Kim, Michael P. Remington and Bhanu Chauhan; "Tetradecachlorocyclohex asilane-Dianion-Containing Compound"; Patent Abstracts of Japan; Publication No. 11171528 A; Publication Date: Jun. 29, 1999; Japan Patent Office, Japan.

Takashi Ouchida; "Formation of Silicon Film"; esp@cenet; Japanese Publication No. JP11079727; Publication Date: Mar. 23, 1999; esp@cenet Database—Worldwide, http://v3.espacenet.com/textdoc?DB= EPODOC&IDX=JP11079727&F=0.

Tsutomu Takadera, Keiichi Fukuyama, Akira Sakawaki, Kotaro Yano and Yutaka Kitsuno; "Method for Forming Silicon Film and Manufacture of Solar Battery"; Patent Abstracts of Japan; Publication No. 200031066 A; Publication Date: Jan. 28, 2000; Japan Patent Office, Japan.

Keiichi Fukuyama, Tsutomu Takadera and Masabumi Shimizu; "Formation of Silicon Film"; esp@cenet; Japanese Publication No. JP2000007317; Publication Date: Jan. 11, 2000; esp@cenet Database—Worldwide, http://v3.espacenet.com/textdoc?DB=EPODOC&IDX=JP2000007317&F=0.

Masahiro Furusawa, Satoru Miyashita, Kazuo Yudasaka, Tatsuya Shimoda, Yasuaki Yokoyama, Yasuo Matsuki and Yasumasa Takeuchi; "Formation Method of Silicon Thin Film"; Patent Abstracts of Japan; Publication No. 2002203794 A; Publication Date: Jul. 19, 2002; Japan Patent Office, Japan.

Kouji Shiho and Hitoshi Kato; "Method of Forming Silicon Oxide Film and Composition Used for Forming the Same"; esp@cenet; Japanese Publication No. JP2002246384; Publication Date: Aug. 30, 2002; esp@cenet Database—Worldwide, http://v3.espacenet.com/textdoc?DB=EPODOC&IDX=JP2002246384&F=0.

Kouji Shiho and Hitoshi Kato; "Production Method of Solar Cell and Composition Therefor"; esp@cenet; Japanese Publication No. JP2003124486; Publication Date: Apr. 25, 2003; esp@cenet Database—Worldwide, http://v3.espacenet.com/textdoc?DB=EPODOC&IDX=JP2003124486&F=0.

Takashi Aoki, Masahiro Furusawa, Yasuo Matsuki, Haruo Iwazawa and Yasumasa Takeuchi; "Higher Order Silane Composition and Process for Forming Silicon Film Using the Same"; esp@cenet; Japanese Publication No. JP2003313299; Publication Date: Nov. 6, 2003; esp@cenet Database—Worldwide, http://v3.espacenet.com/textdoc?DB=EPODOC&IDX=JP2003313299&F=0.

Takashi Aoki, Masahiro Furusawa and Kazuo Yudasaka; "Method for Manufacturing Device, Device and Electronic Apparatus"; esp@cenet; Japanese Publication No. JP2003318120; Publication Date: Nov. 7, 2003; esp@cenet Database—Worldwide, http://v3.espacenet.com/textdoc?DB=EPODOC&IDX=JP2003318120&F=0.

Kouji Shiho and Hitoshi Kato; "Method for Forming Silicon Film or Silicon Oxide Film and Composition for Them"; esp@cenet; Japanese Publication No. JP2003055556; Publication Date: Feb. 26, 2003; esp@cenet Database—Worldwide, http://v3.espacenet.com/textdoc?DB=EPODOC&IDX=JP2003055556&F=0.

Hitoshi Kato and Kouji Shiho; "Forming Method for Silicon Oxide Film and Composition for Formation"; esp@cenet; Japanese Publication No. JP20030922297; Publication Date: Mar. 28, 2003; esp@cenet Database—Worldwide, http://v3.espacenet.com/textdoc?DB=EPODOC&IDX=JP2003092297&F=0.

Takashi Aoki; "Method of Manufacturing Transistor, Electro-Optical Device and Electronic Apparatus"; esp@cenet; Japanese Publication No. JP2004311945; Publication Date: Nov. 4, 2004; esp@cenet Database—Worldwide, http://v3.espacenet.com/textdoc?DB=EPODOC&IDX=JP2004311945&F=0.

Takashi Aoki; "Method of Preparing Higher Order Silane Solution, Method of Forming Silicon Film, Silicon Film, Thin Fil Transistor (TNT), and Electro-Optic Device"; Patent Abstracts of Japan; Publication No. 2005-219981; Publication Date: Aug. 18, 2005; Japan Patent Office, Japan.

Ryuji Sato, Yasuo Nomura, Masashi Nakajima and Yoshiharu Okumura; "Polymerization Catalyst of Hydrosilane"; Patent Abstracts of Japan; Publication No. 04-334551; Publication Date: Nov. 20, 1992; Japan Patent Office, Japan.

Tamejirou Hiyama and Yasuo Hatanaka; "Production of Alpha,Omega-Dihydropolysilane"; Patent Abstracts of Japan; Publication No. 05-230219; Publication Date: Sep. 7, 1993; Japan Patent Office, Japan.

Jiyon Fuiritsupu, Jiyon Toritsukaa Maikeru and Jiyon Kingusuton Tooma Maikeru; "Synthesis of Polysilane"; esp@cenet; Japanese Publication No. JP57027915; Publication Date: Feb. 15, 1982; esp@cenet Database—Worldwide, http://v3.espacenet.com/textdoc?DB=EPODOC&IDX=JP57027915&F=0.

Kotaro Yano, Yutaka Kitsuno, Shoichi Tazawa and Keiji Kawasaki; "Higher Order Silane Containing Solution for Forming Silicon Film"; Patent Abstracts of Japan; Publication No. 06191821A; Publication Date: Jul. 12, 1994; Japan Patent Office, Japan.

Yukio Nishimura, Hiroshi Matsuda, Masahiro Haruta, Yutaka Hirai, Takeshi Eguchi and Takashi Katagiri; "Deposition Film Forming Method"; Patent Abstracts of Japan; Publication No. 60242612 A; Publication Date: Dec. 2, 1985; Japan Patent Office, Japan.

Masaya Fujino and Nobuo Matsumoto; "Polymeric Semiconductor"; (C) 1986, JPO&Japio; Publication No. JP 61200130 A; Publication Date: Sep. 4, 1986; Japan Patent Office, Japan.

Kotaro Yano, Yutaka Kitsuno, Akira Sakawaki and Keiji Kawasaki; "Formation of Silicon Membrane"; Patent Abstracts of Japan; Publication No. 07267621 A; Publication Date: Oct. 17, 1995; Japan Patent Office, Japan.

Tatsuro Beppu, Shuji Hayase, Toshiro Hiraoka, Atsushi Kamata and Kenji Sano; "Semiconductor Film Forming Method and Solar Cell Manufacturing Method"; Patent Abstracts of Japan; Publication No. 09-237927; Publication Date: Sep. 9, 1997; Japan Patent Office, Japan.

Yutaka Kitsuno, Kotaro Yano, Akira Sakawaki and Keiji Kawasaki; "Method for Forming Poly Crystal Silicon Film"; Patent Abstracts of Japan; Publication No. 09045922 A; Publication Date: Feb. 14, 1997; Japan Patent Office, Japan.

Shunichi Seki, Tatsuya Shimoda, Satoru Miyashita, Masahiro Furusawa, Ichio Yudasaka, Yasuo Matsuki and Yasumasa Takeuchi; "Method fof Forming a Silicon Film and Ink Composition for Ink Jet"; esp@cenet; World Publication No. WO0059014 (A1); Publication Date: Oct. 5, 2000; esp@cenet Database—Worldwide, http://v3.espacenet.com/publication Details/biblio?KC=A1&date=20001005 &NR=0059014.

Yasuo Matsuki; "Process for the Formation of Silicon Oxide Films"; esp@cenet; World Publication No. WO0059022 (A1); Publication Date: Oct. 5, 2000; esp@cenet Database—Worldwide, http://v3.espacenet.com/publicationDetails/biblio?KC=A1&date=20001005 &NR=0059022.

Ichio Yudasaka, Tatsuya Shimoda and Shunichi Seki; "Method of Manufacturing Thin-Film Transistor"; esp@cenet; World Publication No. WO0059041 (A1); Publication Date: Oct. 5, 2000; esp@cenet Database—Worldwide, http://v3.espacenet.com/publicationDetails/biblio?KC=A1&date=20001005 &NR=0059041.

Haruo Iwasawa, Daohai Wang, Yasuo Matsuki and Hitoshi Kato; "Silane Polymer and Method for Forming Silicon Film"; esp@cenet; World Publication No. WO2004110929 (A1); Publication Date: Dec. 23, 2004; esp@cenet Database—Worldwide, http://v3.espacenet.com/publicationDetails/biblio?KC=A1&date=20041223 &NR=20041. . . .

John Boyd; "Epson Succeeds in Printing Transistors with Liquid Silicon"; Technolgy Newsline; May 18, 2006; No. 18; 2 pages; Seiko Epson Corp.

Vladimir K. Dioumaev and John F. Harrod; "A Systematic Analysis of the Structure-Reactivity Trends for Some 'Cation-Like' Early Transition Metal Catalysts for Dehydropolymerization of Silanes"; Journal of Organometallic Chemistry; 1996; pp. 133-143; vol. 521; Elsevier Science S.A., Austria.

F. Feher, P. Plichta and R. Guillery; "Beitrage zur Chemie des Siliciums und Germaniums XIII uber die Darstellung Neuer Phenylsilane"; Tetrahedron Letters; Jun. 10, 1970; pp. 2889-2893; No. 33; Pergamon Press, Great Britain.

F. Feher, P. Plichta and R. Guillery; "Beitrage zur Chemie des Siliziums und Germaniums XIV uber die Umsetzung Von Kaliumsilyl mit Phenylbromsilanen und Phenylbromgermanen Darstellung Von Phenylsilylkalium"; Tetrahedron Letters; Oct. 6, 1970; pp. 4443-4447; No. 51; Pergamon Press, Great Britain.

Karl Hassler and Wolfgang Koll; "Synthese und Eigenschaften chlorierter und bromierter Aryltrisilane und Aryltetrasilane"; Journal of Organometallic Chemistry; 1997; pp. 135-143; vol. 538; Elsevier Science S.A., Austria.

Karl Hassler, Ulrike Katzenbeisser and Barbara Reiter; "Verbesserte Synthesen von Phenyltrisilanen"; Journal of Organometallic Chemistry; 1994; pp. 193-196; vol. 479; Elsevier Science S.A., Austria.

E Hengge and H. Firgo; "An Electrochemical Method for the Synthesis of Silicon-Silicon Bonds"; Journal of Organometallic Chemistry; 1981; pp. 155-161; vol. 212; Elsevier Sequoia S.A., The Netherlands.

Uwe Herzog and Robert West; "Heterosubstituted Polysilanes"; Macromolecules; 1999; pp. 2210-2214; vol. 32; American Chemical Society, United States.

Robert D. Miller and Josef Michl; "Polysilane High Polymers"; Chemical Reviews; 1989; pp. 1359-1410; vol. 89, No. 6; American Chemical Society, United States.

R. D. Miller and P.K. Jenkner; "Sacrificial Additives in the Wurtz Synthesis of Polysilanes"; Macromolecules; 1994; pp. 5921-5923; vol. 27; American Chemical Society, United States.

R. D. Miller and R. Sooriyakumaran; "Soluble Alkyl Substituted Polygermanes: Thermochromic Behavior"; Journal of Polymer Science: Part A: Polymer Chemistry; 1987; pp. 111-125; vol. 25; John Wiley & Sons, Inc., United States.

R. D. Miller, D. Thompson, R. Sooriyakumaran and G. N. Fickes; "The Synthesis of Soluble, Substituted Silane High Polymers by Wurtz Coupling Techniques"; Journal of Polymer Science: Part A: Polymer Chemistry; 1991; pp. 813-824; vol. 29; John Wiley & Sons, Inc., United States.

Richard T. Oakley, David A. Stanislawski and Robert West; "Cyclic Polysilanes"; Journal of Organometallic Chemistry; 1978; pp. 389-404; vol. 157; Elsevier Sequoia S.A., The Netherlands.

Robin Richter, Gerhard Roewer, Uwe Bohme, Kathleen Busch, Florence Babonneau, Hans Peter Martin and Eberhard Muller; "Organosilicon Polymers-Synthesis, Architecture, Reactivity and Applications"; Applied Organometallic Chemistry; 1997; pp. 71-106; vol. 11; John Wiley & Sons, Ltd., United States.

Tatsuya Shono, Shigenori Kashimura and Hiroaki Murase; "Electroreductive Synthesis of Polygermane and Germane-Silane Copolymer"; J. Chem. Soc., Chem. Commun.; 1992; 2 pages; Dept of Synthetic Chemistry (Kyoto, Japan) and Advanced Technology Center (Osaka, Japan).

Kohei Tamao, Atsushi Kawachi and Yoshihiko Ito; "Coupling of (Amino) alkylchlorosilanes with Lithium: New Access to Symmetrical Di- and Tetrafunctional Alkyldisilanes"; Organometallics; 1993; pp. 580-582; vol. 12, No. 2; American Chemical Society, United States.

T. Don Tilley; "The Coordination Polymerization of Silanes to Polysilanes by a 'σ-Bond Metathesis' Mechanism. Implications for Linear Chain Growth"; Acc. Chem. Res.; 1993; pp. 22-29; vol. 26, No. 1; American Chemical Society, United States.

Wolfram Uhlig; "Synthesis, Functionalization, and Cross-Linking Reactions of Organosilicon Polymers Using Silyl Triflate Intermediates"; Progress In Polymer Science; 2002; pp. 255-305; vol. 27; Elsevier Science S.A., Austria.

Wolfram Uhlig; "Tailor-Made Synthesis of Functional Substituted Oligo- and Polysilanes from Silyl Triflates and (Aminosilyl)Lithium Compounds"; Journal of Organometallic Chemistry; 2003; pp. 70-78; vol. 685; Elsevier Science B.V.

Qingzheng Wang and Joyce Y. Corey; "Dehydrocoupling Reactions of Hydrosilanes with Group 4 Metallocenes Cp2My2 (M = Ti, Zr, Hf, Y = F, OPh, NMe2)"; Canadian Journal of Chemistry; 2000; pp. 1434-1440; vol. 78; NRC Canada.

Robert West; "The Polysilane High Polymers"; Journal of Organometallic Chemistry; 1986; pp. 327-346; vol. 300; Elsevier Sequoia S.A., The Netherlands.

Klaus Kunze et al.; "Silane Compositions, Methods of Making the Same, Method for Forming a Semiconducting and/or Silicon-Containing Film, and Thin Film Structures Formed Therefrom"; U.S. Appl. No. 10/789,317, filed Feb. 27, 2004.

Vladimir Dioumaev et al.; "Doped Polysilanes Compositions Containing the Same, Methods for Making the Same, and Films Formed Therefrom"; U.S. Appl. No. 11/249,167, filed Oct. 11, 2005.

Certified English-language translation of JP-61200130, 13 pages including title page; translation made on Aug. 2008.

Shimoda et al. "Solution-processed silicon films and transistors", Nature, vol. 440, 2006, pp. 783-786.

Kim et al. "The Effect of Ultraviolet Exposure on Solution Process of Silicon Film" Electrochemical and Solid-State Letters, 12, E23-E25, 2009.

POLYSILANE COMPOSITIONS, METHODS FOR THEIR SYNTHESIS AND FILMS FORMED THEREFROM

RELATED APPLICATIONS

This application is a continuation of U.S. patent application Ser. No. 12/343,200, filed Dec. 23, 2008, now U.S. Pat. No. 8,236,916, which is a continuation of U.S. patent application Ser. No. 11/893,054, filed Aug. 13, 2007, now U.S. Pat. No. 7,491,782, which is a divisional of U.S. patent application Ser. No. 11/246,014, filed Oct. 6, 2005, now U.S. Pat. No. 7,485,691, which in turn claims the benefit of U.S. Provisional Application No. 60/617,562, filed Oct. 8, 2004, each of which is incorporated herein by reference in their entireties.

FIELD OF THE INVENTION

The present invention generally relates to the field of polysilanes and methods of making the same. More specifically, embodiments of the present invention pertain to polysilane compounds, compositions and methods for making and using the same.

SUMMARY OF THE INVENTION

Embodiments of the present invention relate to polysilanes, polysilane ink compositions, methods for making the same and methods of making a semiconducting film using the same. The compounds generally comprise a polysilane of the formula $H\text{-}[(AHR)_n\text{-}(c\text{-}A_mH_{pm-2}R'_{rm})_q]\text{-}H$, where each instance of A is independently Si or Ge; each instance of R and R' is independently H, $\text{-}A_bH_{b+1}R^2_b$ (where $R^2$ is H, aryl or substituted aryl), halogen, aryl or substituted aryl, but if $q=0$ and A is Si, R is not phenyl; $(n+b)\geq 10$ if $q=0$, $q\geq 3$ if $n=0$, and $(n+q)\geq 6$ if both n and $q\neq 0$; p is 1 or 2; $(p+r)=2$; and each instance of m is independently from 3 to 12. In general, n, b and/or $q^*m$ may be the number of silicon and/or germanium atoms in the polysilane according to the number average molecular weight (Mn) of the polysilane. The compositions generally comprise the polysilane compound (particularly the polysilanes in which $R=H$ or $\text{-}A_aH_{2a+1}$) and a solvent in which the polysilane is soluble.

One method of making a polysilane generally comprises the steps of (a) combining a silane compound of the formula $AH_aR^1_{4-a}$, the formula $A_kH_gR^{1'}_h$ and/or the formula $c\text{-}A_mH_{pm}R^{1'}_{rm}$ with a catalyst of the formula $R^4_xR^5_yMX_z$ (or an immobilized derivative thereof or which may be synthesized in situ from the corresponding precursors) to form a poly(aryl)silane of the formula $H\text{-}[(AHR^1)_n\text{-}(c\text{-}A_mH_{(pm-2)}R^{1'}_{rm})_q]\text{-}H$, where each instance of A is independently Si or Ge, $a=2$ or 3, and each instance of $R^1$ is independently aryl, substituted aryl, or $\text{-}A_bH_{b+1}R^2_b$ (where $R^2$ is aryl or substituted aryl); $(n+b)\geq 10$ if $q=0$, $q\geq 3$ if $n=0$, and $(n+q)\geq 6$ if both n and $q\neq 0$; k is an integer from 2 to 12, $g\geq 2$ and $(g+h)=2k+2$; p is 1 or 2, m is an integer from 3 to 12, p is 1 or 2, and r is 0 or 1; $R^{1'}$ is the same as $R^1$, except that when $R^1$ is $\text{-}A_bH_{b+1}R^2_b$ or the silane compound of the formula $AH_aR^1_{4-a}$ is substantially absent, $R^{1'}$ may be H; M is a metal selected from the group consisting of Ti, Zr and Hf, $x=1$ or 2, $y=1$, 2 or 3, $z=0$, 1 or 2, $3\leq(x+y+z)\leq 8$, each of the x instances of $R^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of $R^5$ is independently a substituted or non-substituted hydrocarbyl, hydrocarbyloxy, hydrocarbylamino, hydrocarbylsulfido, silyl, germyl, hydride, phosphine, amine, sulfide, carbon monoxide, nitryl, or isonitryl ligand, and X is a halogen; (b) washing the poly(aryl)silane with a washing composition comprising water; and (c) contacting the poly(aryl)silane with an adsorbent sufficient to remove the metal from the poly(aryl)silane. Alternatively, the method may first form a polyarylsilane in catalytic dehydrocoupling step (a), then include the steps of (b') reacting the polyarylsilane with (i) a halogen source and (optionally) a Lewis acid, or (ii) trifluoromethanesulfonic acid (HOTf), to form a halopolysilane; and (c') reducing the halopolysilane with a metal hydride to form the polysilane of the formula $H\text{-}[(AH_2)_n(c\text{-}A_mH_{pm-2})_q]\text{-}H$. This latter embodiment may also produce a polysilane of the formula $H\text{-}[(AH_2)_{n'-s}(AH[A_aH_{2a+1}])_s(c\text{-}A_mH_{pm-2})_q]\text{-}H$, where A, a, m, and p are as described above; n' is independently an integer in the same range as n above; q' is independently an integer in the same range as q above; and s is an integer less than n' (generally from 1 to 3; e.g., 1).

The present invention is directed towards the synthesis of semiconductor inks via dehydrocoupling of (aryl)silanes and/or -germanes. Such synthesis allows for tuning of the ink properties (e.g., viscosity, boiling point, and surface tension) and for deposition of silicon films or islands by spincoating, inkjetting, dropcasting, etc., with or without the use of UV irradiation. Thus, the invention further relates to a method of making or forming a semiconductor film from the present ink composition, comprising the steps of: (A) spin-coating or printing the composition onto a substrate (optionally, with simultaneous or immediately subsequent UV irradiation); (B) heating the composition sufficiently to form an amorphous, hydrogenated semiconductor; and (C) annealing and/or irradiating the amorphous, hydrogenated semiconductor sufficiently to at least partially crystallize and/or reduce a hydrogen content of the amorphous, hydrogenated semiconductor and form the semiconductor film.

These and other advantages of the present invention will become readily apparent from the detailed description of preferred embodiments below.

DETAILED DESCRIPTION OF THE PREFERRED EMBODIMENTS

Figure 1:
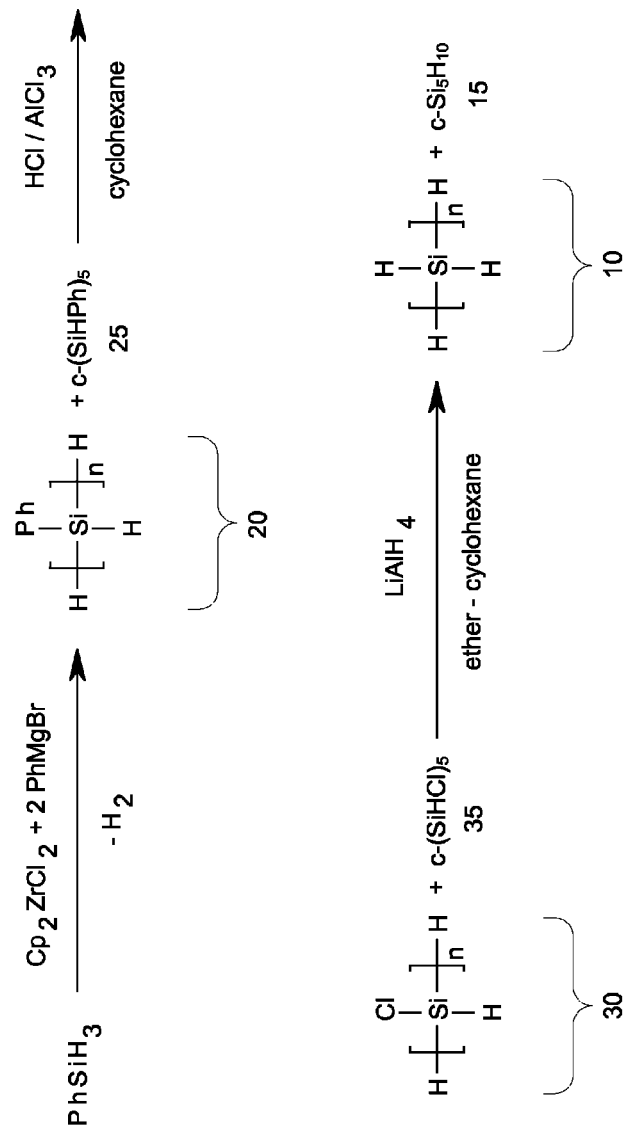
FIG. 1 is a diagram showing a first approach for the synthesis of polysilanes from arylsilane monomers by catalytic dehydrocoupling, halogenation, and reduction.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

For the sake of convenience and simplicity, the terms "$C_a$-$C_b$ alkyl," "$C_a$-$C_b$ alkoxy," etc., shall refer to both branched and unbranched moieties, to the extent the range from a to b covers 3 or more carbon atoms. Unless otherwise indicated, the terms "arene," "aryl," and "ar-" refer to both mono- and polycyclic aromatic species that may be unsubstituted or substituted with one or more conventional substituents, to the extent possible and/or applicable. The prefixes "(per)alkyl" and "(per)hydro" refer to a group having from one to all of its bonding sites substituted with alkyl groups or hydrogen atoms, respectively (e.g., "(per)alkylsilyl" refers to a silyl group of n atoms having from 1 to 2n+1 alkyl groups bound thereto). The terms "silane," "polysilane" and "(cyclo)silane" may be used interchangeably herein, and unless expressly indicated otherwise, these terms individually refer to a compound or mixture of compounds that consists essentially of (1) silicon and/or germanium and (2) hydrogen. The terms "arylsilane," "polyarylsilane" and "aryl(cyclo)silane" may be used interchangeably herein, and unless expressly indicated otherwise, these terms refer to a compound or mixture of compounds that contains or consists essentially of units having a silicon and/or germanium atom, a hydrogen atom bound thereto, and an aryl group bound thereto, where the aryl group may be substituted by a conventional hydrocarbon, silane or germane substituent. The term "(aryl)silane" refers to a silane, polysilane or cyclosilane that may or may not contain an aryl or substituted aryl group bound thereto. The prefix "(cyclo)-" generally refers to a compound or mixture of compounds that may contain a cyclic ring, and the prefix "cyclo-" or "c-" generally refers to a compound or mixture of compounds that contain one or more cyclic rings. For the sake of briefness, the terms "halo-," "halide" and grammatical derivations thereof may describe halogens as defined in the Periodic Table of Elements (F, Cl, Br, and I) and halogen-like species (e.g., that form stable monovalent anions) such as methanesulfonate (OMs), trifluoromethanesulfonate (OTf), toluenesulfonate (OTs), etc. Also, the terms "isolating" and "purifying" (and grammatical variations thereof) may be used interchangeably herein, but these terms are intended to have their art-recognized meanings, unless indicated otherwise.

The present invention concerns a polysilane compound, a "liquid silicon" ink composition containing the polysilane, methods for synthesizing the polysilane and for making the ink composition, and methods of using the polysilane and/or ink composition to make a semiconductor film. In general, the polysilane has the formula $H-[(AHR)_n(c-A_mH_{pm-2}R'_{rm})_q]-H$, where each instance of A is independently Si or Ge; each instance of R and R' is independently H, $-A_aH_{a+1}R^2_a$, (where $R^2$ is H, aryl or substituted aryl), halogen, aryl or substituted aryl, but if q=0 and A is Si, R is not phenyl; (n+a)≧10 if q=0, q≧3 if n=0, and (n+q)≧6 if both n and q≠0; p is 1 or 2; (p+r)=2; and each instance of m is independently from 3 to 12. The composition generally comprises the polysilane compound (preferably where R, R' and [to the extent present] $R^2$ are H) and a solvent in which the polysilane is soluble.

Even further aspects of the invention concern methods of making a polysilane generally comprising the steps of (a) combining a silane compound of the formula $AH_aR^1_{4-a}$, the formula $A_kH_gR^{1'}_h$ and/or the formula $c-A_mH_{pm}R^{1'}_{rm}$ with a catalyst of the formula $R^4_xR^5_yMX_z$ (or an immobilized derivative thereof, or which may be synthesized in situ from the corresponding precursors) to form a poly(aryl)silane of the formula $H-[(AHR^1)_n-(c-A_mH_{(pm-2)}R^{1'}_{rm})_q]-H$, where A, $R^1$, k, g, h, p, q, $R^{1'}$, M, $R^4$, $R^5$, x, y, z, and X are as described herein, and a=2 or 3; (b) washing the poly(aryl)silane with a washing composition comprising water; and (c) contacting the poly(aryl)silane with an adsorbent sufficient to remove the metal from the poly(aryl)silane. Alternatively, the method may first form a polyarylsilane in accordance with step (a), then include the steps of (b') reacting the polyarylsilane with (i) a halogen source and (optionally) a Lewis acid, or (ii) trifluoromethanesulfonic acid (HOTf), to form a halopolysilane; and (c') reducing the halopolysilane with a metal hydride to form the polysilane of the formula $H-[(AH_2)_n-(c-A_mH_{pm-2})_q]-H$.

The invention further relates to a method of making or forming a semiconductor film from the present ink composition, comprising the steps of: (A) spin-coating or printing the composition onto a substrate (optionally, with simultaneous or immediately subsequent UV irradiation); (B) heating the composition sufficiently to form an amorphous, hydrogenated semiconductor; and (C) annealing and/or irradiating the amorphous, hydrogenated semiconductor sufficiently to at least partially crystallize and/or reduce a hydrogen content of the amorphous, hydrogenated semiconductor and form the semiconductor film.

The invention, in its various aspects, will be explained in greater detail below with regard to exemplary embodiments.

An Exemplary Polysilane

In one aspect, the present invention relates to a polysilane having the formula $H-[(AHR)_n(c-A_mH_{pm-2}R'_{rm})_q]-H$, where each instance of A is independently Si or Ge; each instance of R and R' is independently H, $-A_bH_{b+1}R^2_b$ (where $R^2$ is H, aryl or substituted aryl), halogen, aryl or substituted aryl, but if q=0 and A is Si, R is not phenyl; (n+b)≧10 if q=0, q≧3 if n=0, and (n+q)≧6 if both n and q≠0; p is 1 or 2; (p+r)=2; and each instance of m is independently from 3 to 12. In preferred embodiments, the polysilane has the formula $H-(AHR)_n-H$ (i.e., where q=0) or $H-(c-A_mH_{2m-2})_q-H$ (i.e., where n=0). However, as will be explained below (particularly with regard to FIG. 4), polysilanes having both cyclic blocks and linear/branched chains are contemplated. Thus, "n" and "q*m" may represent an average number of silicon and/or germanium atoms in the linear polysilane and in the polycyclosilane, respectively, according to or calculated from the number average molecular weight (Mn) of the polysilane. Furthermore, "n" may represent one or more blocks of substantially linear or branched chains of silicon atoms in the polysilane. Thus, in general, the polysilane may comprise a homopolymer of repeating -(-AHR—)—, -(-$A_kH_{2k}$—)— or -(c-$A_mH_{2m-2}$)— units, or a block copolymer comprising one or more blocks of -(-AHR—)—, -(-$A_kH_{2k}$—)— and/or -(c-$A_mH_{2m-2}$)— units, each of which may include one or more such units in a given block.

A first exemplary polysilane has the formula H-(AHR)$_n$—H, where each instance of A is independently Si or Ge; each instance of R is independently H, halogen, aryl, substituted aryl, or -$A_bH_{b+1}R^2{}_b$ (where $R^2$ is H, aryl or substituted aryl), but if A is Si, R is not phenyl; and (n+b)≧10. In general, the polysilane has a linear structure (i.e., where R is H, halogen, aryl when at least one A is Ge and aryl other than phenyl when A is Si only, or substituted aryl), but branched analogs (i.e., where R is -$A_bH_{b+1}R^2{}_b$) are possible. Generally, such branched analogs will be present in a mixture with one or more linear polysilanes. In general, (n+b) and/or (n+qm) represent an average number of silicon and/or germanium atoms in the product mixture, and in most cases, that average number is less than or equal to about 50. For example, when the polysilane is linear, n≦50. However, under typical conditions and/or using certain known catalysts and/or monomers, (n+b) is more typically ≦25 or 30.

In certain embodiments of the polysilane of H-(AHR)$_n$—H, R is H, Cl, or tolyl (preferably H), and A is Si. However, in other embodiments, at least one A is Ge, and R may be phenyl. In such an embodiment, the polygermasilane is essentially a random and/or statistical mixture of polysilanes, polygermanes and polygermasilanes containing a proportion or ratio of germanium-to-silicon atoms that substantially corresponds to the proportion or ratio of the germanium monomer to silicon monomer in the mixture of starting materials, as may be more fully explained below.

In another aspect, the polysilane has the formula H-(c-$A_mH_{2m-2}$)$_q$—H, where q≧3 (e.g., from 3 to 10); and each instance of m is independently from 3 to 12. In particular, m is generally from 5 to 8, and typically, most instances (e.g., more than 50%, 70% or 80%) of m will predominantly be 5.

The structure and nature of the present poly(aryl)silanes and poly(halo)silanes may be better understood with reference to some exemplary methods for their synthesis.

An Exemplary Method of Making Polyarylsilanes

In general, poly- and oligo-hydrosilane and -hydrogermane compounds for semiconductor inks can be synthesized by dehydrocoupling of arylhydrosilanes and/or arylhydrogermanes ($R^1AH_3$ or $R^1{}_2AH_2$, where $R^1$ is aryl and A=Si or Ge, to form linear, branched, cyclic, and/or caged arylhydrosilanes and/or arylhydrogermanes), followed by Lewis acid-catalyzed cleavage of the aryl groups and hydride reduction to yield linear, branched, cyclo-, and/or caged polysilanes, polygermanes or polysilagermanes. This aspect of the invention focuses on dehydrocoupling of arylhydrosilanes and/or arylhydrogermanes ($R^1AH_3$, where $R^1$ is aryl and A=Si or Ge).

Dehydrocoupling of arylhydrosilanes using titanium (Ti), zirconium (Zr), hafnium (Hf), neodymium (Nd) and uranium (U) catalysts is known (see, e.g., T. D. Tilley, *Acc. Chem. Res.* 1993, vol. 26, pp. 22-29; V. K. Dioumaev and J. F. Harrod, *J. Organomet. Chem.* vol. 521 [1996], pp. 133-143; and Q. Wang and J. Y. Carey, *Can. J. Chem.* vol. 78 [2000], pp. 1434-1440). In part, the present invention relates to use of this approach to synthesize novel polyarylhydrosilanes, -germanes and/or -silagermanes, and to an improved method for synthesizing polyarylhydrosilanes, -germanes and/or -silagermanes that eliminates the metal catalyst to a significantly greater degree than alternative approaches, thereby significantly improving the stability of subsequently-produced polyhydrosilanes, -germanes and/or -sila-germanes.

Thus, in one aspect, the present invention relates to a method of making a polysilane, comprising (a) combining a silane compound of the formula $AH_aR^1{}_{4-a}$, the formula $A_kH_gR^1{}_h$ and/or the formula c-$A_mH_{pm}R^{1'}{}_{rm}$ with a catalyst of the formula $R^4{}_xR^5{}_yMX_z$ (or an immobilized derivative thereof, or which can be synthesized in situ from corresponding precursors) to form a poly(aryl)silane of the formula H-[(AHR$^1$)$_n$-(c-$A_mH_{(pm-2)}R^{1'}{}_{rm}$)$_q$]—H, where each instance of A is independently Si or Ge, a=2 or 3, and each instance of $R^1$ and $R^{1'}$ is independently aryl, substituted aryl, or -$A_bH_{b+1}R^2{}_b$ (where $R^2$ is aryl or substituted aryl); (n+b)≧10 if q=0, q≧3 if n=0, and (n+q)≧6 if both n and q≠0; k is an integer of from 2 to 12, g≧2 and (g+h)=2k+2; p is 1 or 2, m is an integer of from 3 to 12, p is 1 or 2, and r is 0 or 1; $R^{1'}$ is the same as $R^1$, except that when $R^1$ is -$A_bH_{b+1}R^2{}_b$, $R^{1'}$ may be H; M is a metal selected from the group consisting of Ti, Zr and Hf, x=1 or 2, y=1, 2 or 3, z=0, 1 or 2, 3≦(x+y+z)≦8, each of the x instances of $R^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of $R^5$ is independently a substituted or non-substituted hydrocarbyl, hydrocarbyloxy, hydrocarbylamino, hydrocarbylsulfido, silyl, (per)alkylsilyl, germyl, (per)alkylgermyl, hydride, phosphine, amine, sulfide, carbon monoxide, nitryl, or isonitryl ligand, and X is a halogen; (b) washing the poly(aryl)silane with a washing composition comprising water; and (c) contacting the poly(aryl)silane with an adsorbent sufficient to remove the metal (i.e., from the catalyst) from the poly(aryl)silane.

In the first exemplary embodiment of the present method, the silane compound has the formula $AH_aR^1{}_{4-a}$. In preferred implementations of this embodiment, A is Si, $R^1$ is phenyl or tolyl, and/or a is 3. However, compounds of the formula $A_kH_gR^1{}_h$ (particularly where k is an integer of at least 2, g=k, [k+2], 2k or [2k+2], and h=0, 2, or k) are likely to be present in the dehydrocoupling reaction mixture. As a result, the present method contemplates use of compounds of the formula $A_kH_gR^1{}_h$ for making poly(aryl)silanes.

Preferably, the metal M in the dehydrocoupling catalyst is Zr or Hf. These metals tend to provide a sufficient balance between dehydrocoupling rate or activity, poly(aryl)silane molecular weight and content of cyclosilane by-products (e.g., Hf generally produces a higher proportion of linear polysilane products than Zr). In various embodiments, x is 2 and $R^4$ is cyclopentadienyl (Cp), permethyl-cyclopentadienyl (Cp*), indenyl or fluorenyl (Fl). Having at least one bulky or substituted cyclopentadienyl ligand (e.g., Cp*, indenyl or fluorenyl) tends to promote dehydrocoupling by reducing a tendency of the catalyst to dimerize, but the catalyst is not at all required to have such a ligand. Also, in various embodiments, y is 2 and $R^5$ in the dehydrocoupling catalyst is H, $C_1$-$C_6$ alkyl, $C_6$-$C_{12}$ aryl, $SiR^2{}_3$, or $Si(SiR^2{}_3)_3$, where $R^2$ is H or $C_1$-$C_4$ alkyl. Such ligands are believed to promote metathesis of Si—H or Ge—H bonds in the starting silane compound.

Generally, the washing composition in this embodiment of the present method comprises deionized water or dilute aqueous acid. For example, the aqueous acids suitable for use in the present method generally include the mineral acids and their equivalents, such as hydrochloric acid, hydrobromic acid, trifluoroacetic acid, and trifluoromethanesulfonic acid. Preferably, the aqueous acid comprises hydrochloric acid. The dilution factor for the washing composition may be from 1:1 to 1:1000 (concentrated mineral acid to water), generally by volume. For example, the dilute aqueous acid may comprise from 0.1 to 10 vol. % (e.g., from 1 to 5 vol. %) of conc. HCl in deionized water. In a preferred implementation, the present washing step comprises washing the poly(aryl)silane one or more times with dilute aqueous acid, followed by washing the acid-washed poly(aryl)silane one or more times with water.

In general, to further remove the metal from the poly(aryl) silane, a solution of the poly(aryl)silane in a suitable organic solvent (typically the washed poly[aryl]silane) is contacted with the adsorbent for a length of time sufficient for the adsorbent to adsorb the metal from the catalyst. The adsorbent generally comprises a chromatography gel or finely divided silicon and/or aluminum oxide that is substantially unreactive with the polyarylsilane. Examples of suitable adsorbents include silica gel, alumina, FLUORISIL, and CELITE. In one embodiment, such contacting comprises passing the poly(aryl)silane through a column packed with the adsorbent. Alternatively, a solution of the poly(aryl)silane may be mixed with the adsorbent for a length of time sufficient for the adsorbent to adsorb the metal/catalyst from the solution. The adsorbent is generally removed from the adsorption mixture by conventional filtration.

FIG. 1 shows a first exemplary scheme illustrating dehydrocoupling of $PhSiH_3$, followed by Lewis acid-catalyzed chlorination and reduction. Dehydrocoupling of $PhSiH_3$ generally forms polyphenylsilane 20 and a relatively small proportion of cyclic silane compounds such as cyclopentaphenylsilane (c-$(SiHPh)_5$ 25). Although the polyphenylsilane 20 may be separated and/or isolated from the cyclopentaphenylsilane and/or other cyclic silane compounds, the cyclic silane compounds such as c-$(SiHPh)_5$ 25 generally do not affect subsequent steps in the synthesis of polysilanes (see, e.g., the formation of semiconducting films discussed below). The dehydrocoupling reaction evolves hydrogen gas, and thus, tends to be irreversible if the hydrogen gas is removed from the dehydrocoupling reaction vessel. Generally, the polymerization/dehydrocoupling reaction time is from a few hours (e.g., 3, 4, 6 or more hours) to a few days (e.g., 3, 4 or 5 days). The reaction mixture may be formed by dropwise addition of the monomer to a solution of the catalyst, or by mixing the catalyst directly with the monomer. In fact, neat solutions of silane/germane monomer and catalyst tend to provide higher molecular weights (e.g., number average molecular weights, or Mn) of polyarylsilane 20. The reaction temperature is also kept relatively low, from about 0 to about 30° C.), generally to promote higher polyarylsilane 20 molecular weights and/or to reduce the amount of cyclic silane compound. However, in some cases (e.g., when a sterically crowded catalyst and/or monomer is/are used), a higher temperature may be advantageous for increasing the reaction rate.

As shown in FIG. 1, the dehydrocoupling catalyst $Cp_2ZrPh_2$ may be generated in situ from a zirconocene halide (e.g., $Cp_2ZrCl_2$) and an alkyl, aryl or peralkylsilyl metal reagent (e.g., PhMgBr, which can also be generated in situ in accordance with known techniques). Dehydrocoupling catalysts include complexes of Ti, Zr, and/or Hf, in an oxidation state of +4, +3, and/or +2, and having a general formula $R^4{}_xR^5{}_yMX_z$, where M=Ti, Zr, or Hf; x=1 or 2, y=2 or 3, z=0, 1 or 2, $3 \leq (x+y+z) \leq 8$ (which may depend on the coordination sites available on M, as is known in the art), each of the x instances of $R^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of $R^5$ is independently a substituted or non-substituted hydrocarbyl, hydrocarbyloxy, hydrocarbylamino, hydrocarbylsulfido, silyl, germyl, hydride, phosphine, amine, sulfide, carbon monoxide, nitryl, or isonitryl ligand; and X is a halogen (e.g., Cl, Br, OTf, $ClO_4$, etc.).

Further, the metal M, or one or more of the x instances of $R^4$, y instances of $R^5$ or z instances of X, can be independently bound to a silica, alumina, or polymer surface rendering the catalyst heterogeneous. The polymer is typically a hydrocarbon polymer, such as polyethylene, polypropylene, polystyrene, a polyethylene-polypropylene or polyethylene-polystyrene copolymer, etc.

Alternative catalysts can include any conventional dehydrocoupling catalyst, especially those containing a Group 4 element. For example, an Hf analog of the Zr catalyst in FIG. 1 will generally reduce the amount of cyclic silane compounds produced. Also, as mentioned above, metallocene catalysts containing a relatively bulky ligand, such as CpCp*Zr$(SiMe_3)$Ph, may provide higher molecular weight polyphenylsilanes (e.g., having a Mn as high as 5000 Daltons [i.e., n≈25-45], whereas the Mn of the polyphenylsilane 20 produced using $Cp_2ZrPh_2$ is generally around 1200 Daltons [i.e., n≈10-12]). Use of a sterically crowded catalyst like CpCp*Zr$(SiMe_3)$Ph is expected to produce a higher viscosity polysilane ink composition.

The starting material(s) and/or substrates generally include silicon and germanium compounds of the general formula $R^1AH_3$ or $R^1{}_2AH_2$, where A is Si or Ge, and $R^1$ is aryl or substituted aryl. Use of tolylsilane ($CH_3C_6H_4SiH_3$) as a monomer instead of phenylsilane ($PhSiH_3$) may be advantageous for subsequent steps in the polysilane synthesis. Tolylsilane (and oligomers thereof) are generally easier to chlorinate (e.g., cleave the C—Si bond with HCl and a Lewis acid such as $AlCl_3$), thereby presumably reducing aromatic impurities in any subsequently synthesized polysilane.

Typical conditions for dehydrocoupling reaction include a temperature of about ambient or room temperature, a pressure of about atmospheric pressure (or about 1 atm) of inert gas under dynamic conditions (e.g., in a reaction vessel having somewhat free gas out-flow, such as a gas bubbler, generally to allow escape of evolved hydrogen gas). The typical catalyst loading may be >1 mol % (e.g., from 1 to 10 mol %, 2 to 5 mol %, or any range of values therein, relative to the molar quantity of monomer) for dehydrocoupling of arylsilanes and arylgermanes.

The adsorbing step in the present method is generally used to remove the metal of the catalyst (e.g., Zr in FIG. 1) from the polyphenylsilane 20. Conventional chromatography methods using gels, such as FLORISIL, and other gels like silica, alumina, and CELITE are generally suitable. Alternatively, the gel is added to a polyphenylsilane 20 solution and stirred (generally for a length of time sufficient to remove some or substantially all of the metal from the solution), then the gel is generally removed by filtration. Contacting a chromatography gel with a solution of the polyphenylsilane 20 can be substituted by simply passing the solution of polyphenylsilane 20 through a thick pad of the gel.

The solvents used in the procedure are not limited. Cyclohexane, toluene, and diethyl ether are generally preferred, although any solvent or mixture of solvents with relatively low boiling points (e.g., $\leq 100°$ C., $\leq 80°$ C., or $\leq 60°$ C.), compatible with polysilanes, are suitable.

Figure 2:
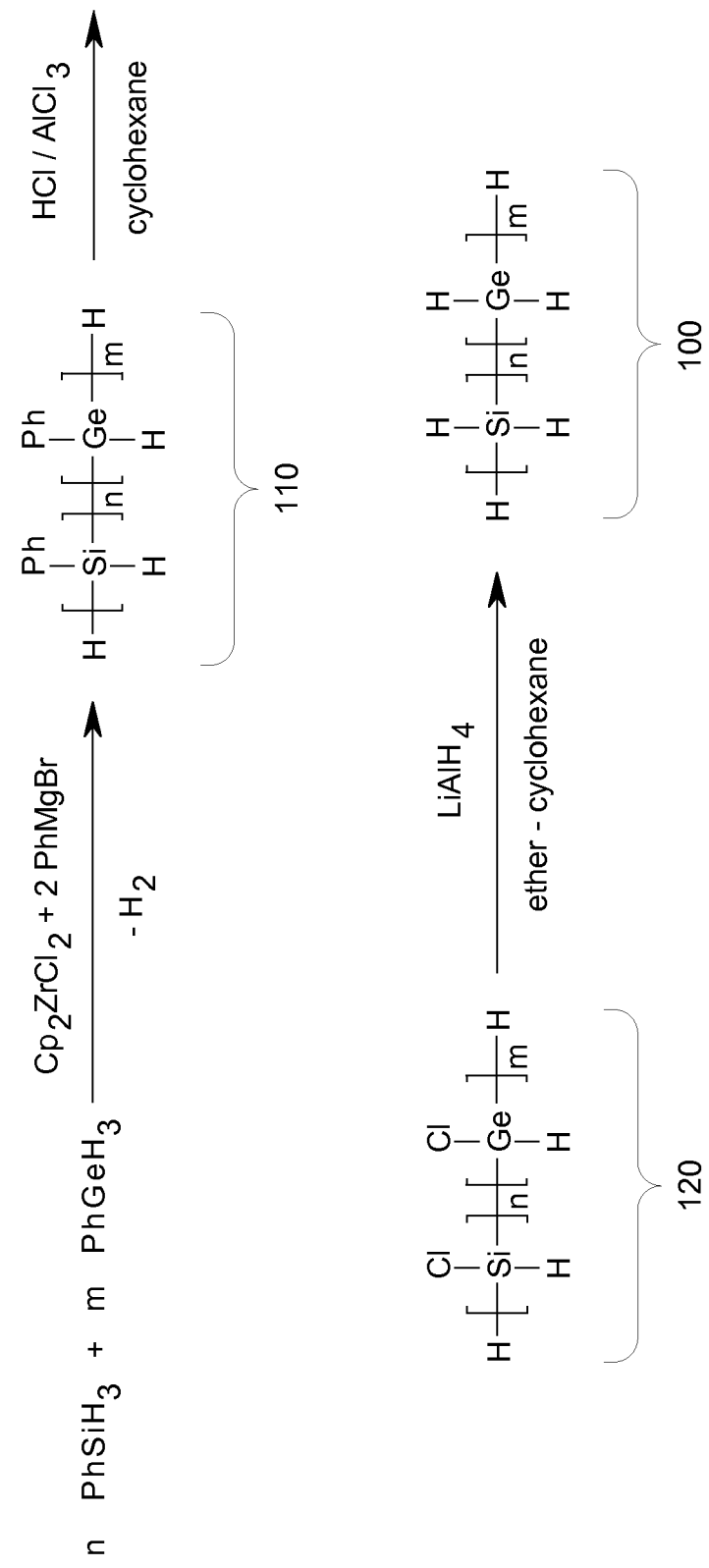
FIG. 2 is a diagram showing a second approach for the synthesis of polysilagermanes from arylsilane and arylgermane monomers by catalytic dehydrocoupling, halogenation, and reduction.

FIG. 2 shows a second exemplary scheme illustrating dehydrocoupling of $PhSiH_3$ and $PhGeH_3$, followed by chlorination and reduction. Generally, a mixture of arylsilane (e.g., $PhSiH_3$) and arylgermane ($PhGeH_3$) are dehydrocoupled using a diaryl-, bis(peralkylsilyl)-, aryl(peralkylsilyl)-, dialkyl- or alkyl(peralkylsilyl)metallocene catalyst such as $Cp_2ZrPh_2$ to provide a polyphenylsilagermane 110 of the formula H—(SiHPh)$_n$(GeHPh)$_m$-H, where (n+m)≧10. In the polyphenylsilagermane 110 product, n and m generally represent a random and/or statistical mixture corresponding to the molar ratio of PhSiH$_3$ to PhGeH$_3$ in the dehydrocoupling reaction mixture. Thus, m may be anywhere from 1 to (n−1), but more typically, the molar ratio of PhSiH$_3$ to PhGeH$_3$ is anywhere from 1:1 to 20:1, and thus, m will typically be an integer of from 1 to n. The product mixture containing polyphenylsilagermane 110 may also include cyclic and linear/branched polyphenylsilanes and -germanes. No significant and/or detectable heterocoupling may occur in such cyclic byproducts in the synthetic approach of FIG. 2.

An Exemplary Method of Making Polysilanes

Cleavage of aryl groups bound to Si or Ge, and reduction of silicon and/or germanium halides and pseudo-halides are generally disclosed in, e.g., U.S. patent application Ser. Nos. 10/789,317, 10/949,013, 10/950,373 and 10/956,714, respectively filed on Feb. 27, 2004, Sep. 24, 2004, Sep. 24, 2004, and Oct. 1, 2004, the relevant portions of which are incorporated herein by reference. Typically, and as shown in FIGS. 1 and 2, this cleavage reaction is conducted with HCl and AlCl$_3$. However, as is also known, a conventional chlorination-based cleavage reaction can be substituted with HBr to obtain a polybromosilane, or with TfOH to obtain a poly(trifluoromethanesulfonyl)silane. Thus, the present invention also relates to the combination of (1) catalytic dehydrocoupling as described above and (2) the cleavage and reduction processes described herein, to synthesize polyhydrosilanes, -germanes and/or -silagermanes.

Thus, in another aspect, the present invention concerns a method of making a polysilane, comprising the steps of (a) combining a silane compound of the formula AH$_a$R$^1_{4-a}$, the formula A$_k$H$_g$R$^{1'}_h$ and/or the formula c-A$_m$H$_{pm}$R$^{1'}_{rm}$ with a catalyst of the formula R$^4_x$R$^5_y$MX$_z$ (or an immobilized derivative thereof) to form a polyarylsilane of the formula H-[(AHR$^1$)$_n$(c-A$_m$H$_{(pm-2)}$R$^{1'}_{rm}$)$_q$]—H as described above, where each instance of A is independently Si or Ge, a=2 or 3, each instance of R$^1$ and R$^{1'}$ is independently aryl, substituted aryl, or -A$_b$H$_{b+1}$R$_b$ (where R is aryl or substituted aryl); (n+b)≧10 if q=0, q≧3 if n=0, and (n+q)≧6 if both n and q≠0; p is 1 or 2; k is an integer of from 2 to 12, g≧2 and (g+h)=2k+2; each instance of m is independently from 3 to 12; M is a metal selected from the group consisting of Ti, Zr and Hf; x=1 or 2; y=1, 2 or 3; z=0, 1 or 2; 3≦(x+y+z)≦8; each of the x instances of R$^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of R$^5$ is independently a substituted or non-substituted hydrocarbyl, hydrocarbyloxy, hydrocarbylamino, hydrocarbylsulfido, silyl, germyl, hydride, phosphine, amine, sulfide, carbon monoxide, nitryl, or isonitryl ligand; and X is a halogen; (b) reacting the polyarylsilane with (i) a halogen source and (optionally) a Lewis acid or (ii) trifluoromethanesulfonic acid (HOTf), to form a halopolysilane; and (c) reducing the halopolysilane with a metal hydride to form a polysilane of the formula H-[(AH$_2$)$_n$(c-A$_m$H$_{pm-2}$)$_q$]—H.

Generally, the method comprises combining a silane compound of the formula AH$_a$R$^1_{4-a}$ with a catalyst of the formula R$^4_x$R$^5_y$MX$_z$ to form a polyarylsilane of the formula H-(AHR$^1$)$_n$—H. However, as described above, compounds of the formula A$_k$H$_g$R$^{1'}_h$ (particularly where k is an integer of at least 2, g=2, [k+2], 2k or [2k+2], and h=0, 2 or k, depending on the structure of the silane starting compound) are likely to be present in the dehydrocoupling reaction mixture. As a result, the present method contemplates use of compounds of the formula A$_k$H$_g$R$^{1'}_h$ for making polyarylsilanes. Also, in certain embodiments, the method comprises reacting the polyarylsilane with the halogen source and the Lewis acid, wherein the Lewis acid comprises a compound of the formula M$^3_v$X$^2_w$, where M$^3$ comprises a member selected from the group consisting of transition metals and Group IIIA elements; v is 1 or 2; X$^2$ comprises a halogen; and w is any integer up to the number of ligand binding sites available on the v instances of M$^3$. In a preferred embodiment, M$^3$ comprises Al, and X$^2$ is Cl or Br (e.g., Cl, as shown in FIGS. 1-2).

In further embodiments of the present method, the metal hydride comprises a compound of the formula M$^1_a$M$^2_b$H$_c$R$^6_d$, where M$^1$ and M$^2$ are independently first and second metals, each R$^6$ in the metal hydride compound is independently a ligand bound to at least one of M$^1$ and M$^2$ by a covalent, ionic or coordination bond, at least one of a and b is at least 1, c is at least 1, and d is 0 or any integer up to one less than the number of ligand binding sites available on the (a+b) instances of M$^1$ and M$^2$. In certain implementations, the metal hydride comprises a member of the group consisting of lithium aluminum hydride (LAH, as shown in FIGS. 1-2), calcium aluminum hydride, sodium borohydride, aluminum hydride, gallium hydride, and aluminum borohydride.

Referring to FIGS. 1-2, the procedure for Lewis acid-catalyzed halogenation (e.g., treatment or reaction of polyarylsilane 20 or polyarylsilagermane 110 with HCl and AlCl$_3$ in an inert organic solvent such as cyclohexane) is largely as described in U.S. patent application Ser. No. 10/789,317. However, exemplary variations of the procedure include a halogenation (e.g., chlorination) by bubbling HX gas (e.g., dry HCl) through a solution of polyarylsilane 20 or polyarylsilagermane 110 and Lewis acid for a length of time of from 30 min. to about 6 hours to form polychlorosilane 30 or polychlorosilagermane 120, respectively, and reduction using a metal hydride reducing reagent (not limited to lithium aluminum hydride [LAH], although LAH as shown in FIGS. 1 and 2 is a preferred metal hydride reducing reagent) for a length of time of from about 1 hour, 2 hours or 4 hours to about 8, 12, or 16 hours (e.g., overnight). Other exemplary metal hydride reducing agents are disclosed in U.S. patent application Ser. Nos. 10/789,317, 10/949,013, 10/950,373 and 10/956,714, the relevant portions of which are incorporated herein by reference. Also, the reagent addition sequence preferably comprises adding a solution of metal hydride (e.g., LAH) in an inert organic solvent (e.g., dry diethyl ether) to a stirred solution of polychlorosilane 20 or polychlorosilagermane 120. Workup is generally as described in U.S. patent application Ser. Nos. 10/789,317, 10/949,013, 10/950,373 and 10/956,714, the relevant portions of which are incorporated herein by reference.

A Second Exemplary Method for Making Oligo- and/or Polysilanes

Figure 3:
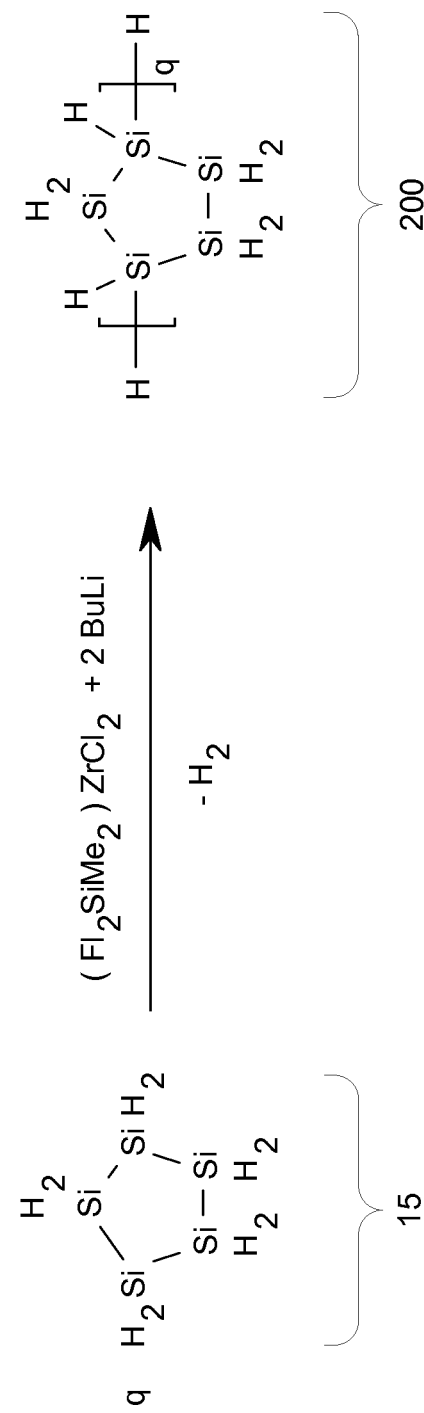
FIG. 3 is a diagram showing an approach for the synthesis of polycyclosilanes from cyclosilane monomers by catalytic dehydrocoupling alone.

In another aspect, the present invention concerns a method of making oligo- and/or polysilanes that includes simply a dehydrocoupling step (e.g., dehydrocoupling of perhydrosilanes and/or perhydrogermanes; e.g., linear, branched, cyclo-, or caged hydrosilanes and/or hydrogermanes), such as the exemplary reaction scheme of FIG. 3. FIG. 3 shows an exemplary scheme illustrating dehydrocoupling of cyclo-Si$_5$H$_{10}$ 15 to form poly(cyclopentasilane) 200. Generally, the same dehydrocoupling catalyst (e.g., α-fluorenyl-α,α-dimethylsilylfluorenyl dibutylzirconium, or [Fl$_2$SiMe$_2$]ZrBu$_2$, generated in situ as shown in FIG. 3) as described above may be used for dehydrocoupling cyclosilanes. For dehydrocoupling of c-Si$_5$H$_{10}$, typical catalyst loading may be <0.1 mol % (e.g., from 0.0001 to 0.1 mol %, 0.001 to 0.05 mol %, or any range of values therein), relative to the amount of monomer (e.g., c-Si$_5$H$_{10}$).

Thus, the present invention further concerns a method of making an oligo- and/or polysilane, comprising (1) combining a silane compound of the formula c-$A_mH_{pm}$ and/or the formula $A_kH_{2k+2}$ with a catalyst of the formula $R^4_xR^5_yMX_z$ (or an immobilized derivative thereof, or which may be synthesized in situ from corresponding precursors) to form a polysilane of the formula H-$(A_kH_{2k})_{q'}$-(c-$A_mH_{pm-2})_q$—H, where each instance of A is independently Si or Ge, q'+q≧3, p is 1 or 2, k is an integer of from 2 to 12, m is an integer of from 3 to 12, and M, x, y, z, $R^4$, $R^5$, and X are as described above; (2) washing the polysilane with a washing composition comprising water; and/or (3) contacting the polysilane with an adsorbent sufficient to remove the metal from the polysilane.

In further embodiments of the approach exemplified in FIG. 3, A is independently Si or Ge, q≧3, p is 1 or 2, and/or m is from 3 to 12 (preferably from 5 to 8). In addition, linear and/or branched silanes of the general formula $A_kH_{2k+2}$ (where k is from 1 to 12, preferably from 5 to 10 [e.g., for homogeneous synthesis] or from 1 to 4 [e.g., for heterogeneous synthesis]) may be added to the dehydrocoupling reaction mixture to form polysilanes of the formula H-[(AHR*)$_n]_t$-(c-$A_mH_{pm-2})_q$]—H, where R* is H or -$A_bH_{2b+1}R_b$ (preferably H), each of the t instances of n are independently from 1 to 12 (preferably from 3 to 12, more preferably from 5 to 10), each of the t*n instances of b are independently from 1 to 6 (preferably from 1 to 4), t*(n+b)≧4 (preferably ≧6 and more preferably ≧10), and m, p and q are as described above.

A Third Exemplary Method for Making Oligo- and/or Polysilanes

Figure 4:
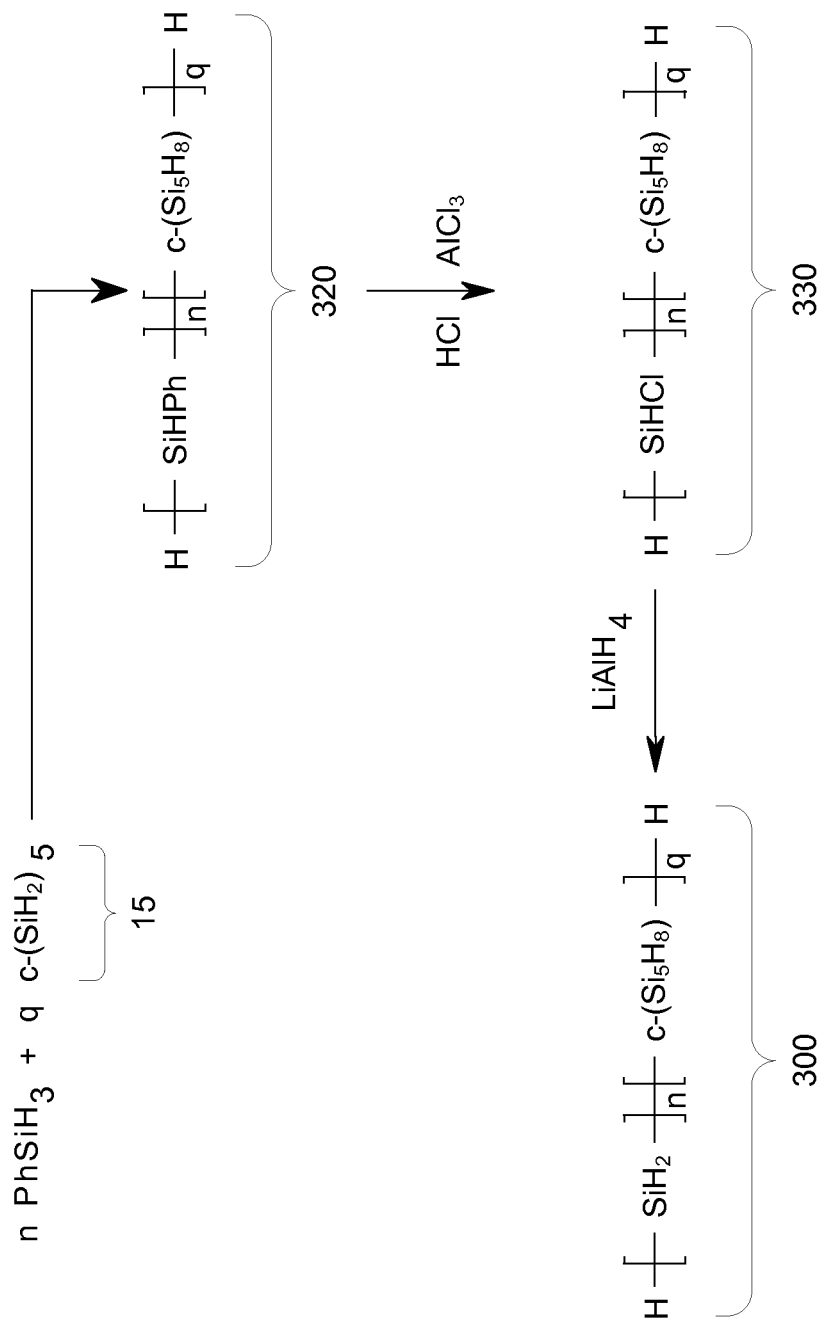
FIG. 4 is a diagram showing an approach for the synthesis of poly(cyclo)silanes from arylsilane and cyclosilane monomers by catalytic dehydrocoupling, halogenation, and reduction.

In another aspect, the present invention concerns oligo- and/or polysilanes containing both linear and cyclic portions and a method of making the same, based on catalytic dehydrocoupling (e.g., dehydrocoupling of [aryl]silanes and/or [aryl]germanes with cyclosilanes and/or cyclogermanes), such as the exemplary reaction scheme of FIG. 4. FIG. 4 shows an exemplary scheme illustrating dehydrocoupling of phenylsilane (PhSiH$_3$) with cyclo-Si$_5$H$_{10}$ 15 to form block copolymer or linear/branched poly(phenylsila)(cyclopentasilylene) 320. Generally, the same dehydrocoupling catalyst (e.g., bis[cyclopentadienyl]diphenylzirconium or [Fl$_2$SiMe$_2$] ZrBu$_2$, as shown in FIGS. 1-3) as described above may be used for dehydrocoupling arylsilanes with cyclosilanes. Linear or branched perhydrosilanes can be substituted for or added to the cyclosilanes, to provide a greater degree of branching or to possibly increase the average number of silicon atoms in the polymer/oligomer. Also, cyclosilanes with an exocyclic silyl group (e.g., cyclo-[(SiPhH)$_4$SiH]—[SiH$_3$]) are also contemplated for use in the invention, and this are encompassed by the formula "c-$A_mH_{pm}$." The subscript "n" generally represents an average of the number of silicon atoms in the polysilane, and in this aspect of the invention, further represents two or more blocks of substantially linear or branched silicon chains in the polysilane.

Thus, the present invention further concerns a method of making an oligo- and/or polysilane, comprising (I) combining a silane compound of the formula c-$A_mH_{pm}$ and/or the formula $A_kH_{2k+2}$ with a silane monomer of the formula AH$_3$R$^1$ and a catalyst of the formula $R^4_xR^5_yMX_z$ (or an immobilized derivative thereof, or which may be synthesized in situ from corresponding precursors) to form a block or branched polyarylsilane of the formula H-[(AHR$^1$)$_n]_u$-$(A_kH_{2k})_{q'}$-(c-$A_mH_{pm-2})_q$—H, where each instance of A, R$^1$ and n are as described herein, u=(q'+q) or (q'+q)±1, q'+q≧3, p is 1 or 2, k is an integer of from 2 to 12, m is an integer of from 3 to 12, and M, x, y, z, $R^4$, $R^5$, and X are as described above; (II) reacting the block or branched poly(aryl)silane with (i) a halogen source and (optionally) a Lewis acid or (ii) trifluoromethanesulfonic acid (HOTf), to form a block or branched halopolysilane; and (c) reducing the block or branched halopolysilane with a metal hydride to form a polysilane of the formula H-[(AH$_2$)$_n]_u$-$(A_kH_{2k})_{q'}$-(c-$A_mH_{pm-2})_q$—H. In further embodiments of the approach exemplified in FIG. 4, A is Si, q' is 0, p is 2, and/or m is from 5 to 8 (preferably 5 or 6).

An Exemplary Polysilane Composition and/or Semiconductor Ink

A further aspect of the present invention relates to a composition, comprising the present polysilane and a solvent in which the polysilane is soluble. Preferably, the solvent is one that is easily removed (and/or substantially completely removable) from the composition, and may be selected from the group consisting of linear alkanes, cycloalkanes, polycycloalkanes, (cyclic) siloxanes and fluoroalkanes. Other apolar and/or non-polar solvents (e.g., branched $C_5$-$C_{12}$ alkanes, aliphatic ethers such as di-$C_2$-$C_6$ alkyl ethers, methyl $C_4$-$C_6$ alkyl ethers and di-$C_1$-$C_4$ alkyl $C_2$-$C_6$ alkylene diethers [e.g., glyme], cyclic ethers such as tetrahydrofuran and dioxane, etc.) may be included in compositions suitable for use in the present methods of coating a substrate with a silane film and/or forming a thin film. The (cyclic) siloxane solvents are generally those that are liquid at ambient temperatures (e.g., 15-30° C.), and may be selected from siloxanes of the formula (R$_3$Si)(OSiR$_2$)$_p$(OSiR$_3$) and cyclosiloxanes of the formula (SiR'$_2$O)$_q$, where p is from 0 to 4, q is from 2 to 6 (preferably from 3 to 5), each R and R' is independently H, $C_1$-$C_6$ alkyl, benzyl or phenyl substituted with from 0 to 3 $C_1$-$C_4$ alkyl groups (preferably R and R' are methyl). The fluoroalkane may be selected from $C_3$-$C_8$ fluoroalkanes substituted with from 1 to (2m+2) fluorine atoms and that are liquid at ambient temperatures, where m is the number of carbon atoms in the fluoroalkane. More preferably, the solvent may be selected from the group consisting of $C_6$-$C_{12}$ monocycloalkanes and $C_{10}$-$C_{14}$ di- or tricycloalkanes (e.g., decalin). Preferably, the solvent is a $C_6$-$C_{10}$ cycloalkane (e.g., cyclohexane, cycloheptane, cyclooctane, etc.).

In the present ink composition, the polysilane is present in an amount of from about 0.5 to about 50%, preferably 5 to about 30% (more preferably from about 10 to about 20%) by weight or by volume. Of course, when the polysilane is in a liquid phase at room temperature, it may be used neat if its viscosity (and/or other physical and/or chemical properties) are suitable for printing and/or coating processes. Suitable ink formulations are disclosed in U.S. patent application Ser. Nos. 10/789,274, 10/789,317, 10/949,013, 10/950,373 and 10/956,714, respectively filed on Feb. 27, 2004, Feb. 27, 2004, Sep. 24, 2004, Sep. 24, 2004, and Oct. 1, 2004, the relevant portions of which are incorporated herein by reference. In the present case, the present polysilane may be substituted in part or entirely for the (cyclo)silane and/or hetero (cyclo)silane described in U.S. patent application Ser. Nos. 10/789,274, 10/789,317, 10/949,013, 10/950,373 and 10/956,714.

An Exemplary Method for Making a Semiconductor Film

A further aspect of the invention relates to a method of forming a semiconductor film from the present composition, comprising the steps of (A) spin-coating or printing the composition onto a substrate (optionally, with simultaneous or immediately subsequent UV irradiation); (B) heating the composition sufficiently to form an amorphous, hydrogenated semiconductor; and (C) annealing and/or irradiating the amorphous, hydrogenated semiconductor sufficiently to at least partially crystallize and/or reduce a hydrogen content of the amorphous, hydrogenated semiconductor and form the semiconductor film. Preferably, the method of forming a semiconductor film comprises printing (e.g., inkjetting) the composition onto a substrate (e.g., a conventional silicon wafer, glass plate, ceramic plate or disc, plastic sheet or disc, metal foil, metal sheet or disc, or laminated or layered combination thereof, any of which may have an insulator layer such as an oxide layer thereon), and/or irradiating the amorphous, hydrogenated semiconductor with a sufficient dose of laser radiation to crystallize and/or electrically activate the amorphous, hydrogenated semiconductor and form the semiconductor film.

In the present method, it may be advantageous to irradiate the composition during deposition onto the substrate. In one example, the method comprises irradiating the composition sufficiently to (i) cross-link, isomerize, oligomerize and/or polymerize the (poly)silane, (ii) form a substantially uniform layer on the substrate, the layer comprising the oligo- and/or polysilane, and/or (iii) increase an average molecular weight, increase a viscosity and/or reduce a volatility of the composition (e.g., the [poly]silane). The ultraviolet light may have a bandwidth with an intensity maximum between 200 and 440 nm, between 220 and 400 nm, or between 250 and 380 nm. Generally, as long as the ink composition is irradiated reasonably shortly after deposition (e.g., spincoating), it has a viscosity sufficient to form a film or layer on the substrate that does not bead up, disproportionate or otherwise substantially adversely affect the uniformity of a subsequently formed semiconductor film. Such irradiation of a coated and/or printed film prior to curing may provide further control of the film drying process, e.g., by increasing the viscosity of the ink composition after deposition. For example, the present composition (e.g., prior to deposition) may have a viscosity of from 2.5 to 20 cP, 3 to 12 cP, or any range of values therein.

Suitable methods for forming a semiconductor film are disclosed in U.S. patent application Ser. Nos. 10/789,274, 10/949,013, 11/084,448 and 11/203,563, respectively filed on Feb. 27, 2004, Sep. 24, 2004, Mar. 18, 2005 and Aug. 11, 2005, the relevant portions of which are incorporated herein by reference. In the present case, the present polysilane ink composition may be substituted in part or entirely for the (cyclo)silane and/or hetero(cyclo)silane ink composition described in U.S. patent application Ser. Nos. 10/789,274, 10/949,013, 11/084,448 and 11/203,563. The first heating and/or annealing step may comprise (i) "soft" curing the printed or coated ink composition, generally at a temperature of $\leq 200°$ C., $\leq 150°$ C., $\leq 120°$ C. or any maximum temperature in that range, sufficiently to remove volatile components (e.g., solvent, volatile silane compounds, etc.) and/or to further polymerize the silane film, and (ii) "hard" curing the film, generally at a temperature of $\leq 600°$ C., $\leq 500°$ C., $\leq 450°$ C. or any maximum temperature in that range, sufficiently to form a hydrogenated, amorphous silicon film. Generally, to obtain the most commercially valuable electrical activity and/or characteristics, the film is crystallized by heating in a furnace or irradiating with a dose of laser radiation sufficient to partly or substantially completely crystallize the hydrogenated, amorphous silicon film (e.g., form a polycrystalline silicon film). The use of laser radiation for crystallization advantageously includes a further annealing step to reduce the hydrogen content of the hydrogenated, amorphous silicon film prior to laser irradiation.

The described polysilanes and polysilane inks may also be used for the formation of doped silicon films. For example, an ink composition comprising the present polysilane may be printed or coated (optionally, with simultaneous or immediately subsequent UV irradiation) onto a substrate, converted to an amorphous or (partially) polycrystalline silicon film and subsequently doped, e.g., by conventional ion implantation or other doping technique such as ion showering or use of conventional spin-on-dopants (and optionally, subsequent annealing). Alternatively, the present ink composition may be further mixed with one or more dopants of the formula $D_aH_b$ and/or $D_aR^6{}_{b'}$ (where D is Sb, As, P or B; a is from 1 to 20; b is from 0 to 26; each of the b' instances of $R^6$ is independently H, alkyl, aryl, aralkyl or $AR^{2'}{}_3$, where $R^{2'}$ is hydrogen, alkyl, aryl, aralkyl or $A_yH_{2y+1}$ [e.g., where $1 \leq y \leq 4$, such as $SiH_3$ and $Si(SiH_3)_3$]; and b' is an integer corresponding to the number of binding sites available on the a instances of D) and/or one or more doped silane and/or germane compounds of the formula $(R^{2'}{}_3A)_rA_c(DR^6{}_2)_s$ (where D, a, $R^{2'}$ and $R^6$ are as described for the dopant; c is 1 to 4, r+s=2c+2, and $s \geq 1$ [preferably $s \geq 3$]) in an amount sufficient to provide a predetermined doping level or concentration and/or electrical characteristics in the electrically active film within a predetermined range of values. Such dopants, doped silanes and germanes, and others are disclosed in U.S. patent application Ser. No. 10/949,013, filed on Sep. 24, 2004, the relevant portions of which are incorporated herein by reference.

Coating may comprise spin coating, inkjetting, dip-coating, spray-coating, slit coating, extrusion coating, or meniscus coating the ink composition onto a substrate. Preferably, coating comprises spin coating. Printing may comprise inkjetting or gravure, flexographic, screen or offset printing the ink in locations on the substrate corresponding to active transistor regions. After drying and/or heating the printed/coated film to remove any solvents and/or cure the film, and optionally irradiating the film (e.g., to fix the silanes to the substrate and/or to each other), the resulting semiconductor film/layer generally has an amorphous morphology, and before further processing, it is generally annealed (e.g., to reduce the hydrogen content of the polysilane) and crystallized (e.g., by heating or by laser irradiation; see, e.g., U.S. patent application Ser. Nos. 10/950,373 and 10/949,013, each of which was filed on Sep. 24, 2004, the relevant portions of which are incorporated herein by reference). In many cases, such crystallization will also activate at least some of the added dopant.

One may also induce crystallization (in addition to activating some or all of the dopant) using conventional metal-promoted (re)crystallization. Suitable metal-based crystallization promoters and processes for their use in crystallizing an amorphous semiconductor film (e.g., as formed from semiconductor nanoparticles containing Si and/or Ge) may be disclosed in U.S. Pat. No. 7,078,276, the relevant portions of which are incorporated herein by reference.

EXPERIMENTAL EXAMPLES

General Procedures

Standard Schlenk techniques were used for all synthesis and sample manipulations. A grease-free reaction setup utilizing threaded Teflon stopcocks was generally used to reduce contamination. Glassware was dried overnight at 120° C. in an oven before use. $^1H$ NMR and $^{29}Si$ NMR were measured by Acorn INC using $d_6$-benzene or $d_{12}$-cyclohexane as solvent. The molecular weight of polyphenylsilane was analyzed by Scientific Polymer Products, Inc., using Phenomenex phenogel columns. Elemental analyses were carried out by Desert Analytics.

Solvents and Reagent Purification.

Toluene was purified by shaking twice with cold conc. $H_2SO_4$ (100 ml acid per L solvent), once or twice with water, once with aqueous 5% $NaHCO_3$, and again with water. Carbonyl-containing impurities were then removed by percolation through a Celite column impregnated with 2,4-dinitrophenylhydrazine, phosphoric acid and $H_2O$. The washed toluene was then dried over 4 Å molecular sieves overnight, and was distilled fresh to remove high boiling point residue.

Cyclohexane was first washed with conc. $H_2SO_4$ until the washings were colorless, followed by washing with alkaline potassium permanganate until the purple color of potassium permanganate did not change. Carbonyl-containing impurities were then removed by percolation through a Celite column impregnated with 2,4-dinitrophenylhydrazine, phosphoric acid and $H_2O$. The washed cyclohexane was then dried with activated 4 Å molecular sieves overnight and distilled over sodium (under argon).

Inhibitor-free diethyl ether was passed through a column of activated alumina (100 g $Al_2O_3$/1 L of ether), dried over lithium aluminum hydride (LAH) overnight, and freshly distilled under argon. DME (1,2-dimethoxyethane) was purified using the same method as for purifying ether.

$PhSiH_3$ (Gelest) was dried over 4 Å molecular sieves overnight, and then distilled under argon. $AlCl_3$ was purified by sublimation at 160° C. under vacuum.

LAH used for the chlorosilane reductions was purified from 1M LAH/ether solution (Aldrich). The purification procedure for obtaining 40 ml of purified 1M LAH ether solution is as follows: 40 ml of purified cyclohexane was added to 40 ml commercial 1 M LAH/ether solution. The mixture was concentrated by removing the ether under vacuum, and at the same time, white LAH precipitated out. The LAH was isolated by centrifugation, decanting the cyclohexane, and washing with 40 ml purified cyclohexane. The obtained white LAH was re-dissolved in 40 ml freshly purified ether, and 40 ml purified cyclohexane was added to the solution. The precipitation, centrifugation, and purified cyclohexane washing steps were repeated again to get purified LAH powder. 36 ml purified ether was added to the purified LAH to make 1M LAH/ether solution.

To obtain high purity polysilane, the purity of the solvents and the commercial LAH/ether solution or LAH powder is important. After employing the solvent and reagent purification procedures described above, alkyl impurities in the polysilane were decreased to less than 0.3% (from 1.4%), as determined by $^1H$ NMR spectroscopy (the chemical shift [or peaks] at 0.9 ppm and 1.3 ppm are assigned to alkyl impurity groups in the polysilane).

Example 1

Synthesis of $Cp_2ZrPh_2$ catalyst $Cp_2ZrCl_2$ (10.18 g, 34.8 mmol) and 80 ml of DME were added to a 1 L Schlenk flask with a thermowell in the glove box. An addition funnel with 25 ml of 3M PhMgBr in ether was connected to the Schlenk flask. The setup was then connected to the Schlenk line. PhMgBr in ether was added slowly to a vigorously stirred solution maintained at a temperature of from 0 to 10° C. The reaction mixture was stirred overnight at room temperature after the addition. Thereafter, 80 ml of toluene was added to the reaction mixture and stirred for 30 minutes in the glove box. After removing the reaction residue by filtration, the dark green solution was dried under vacuum at 20° C. The resulting brown product was washed three times with 40 ml ether. 7.28 g of final product was obtained after drying overnight under vacuum (yield: 56%). The $Cp_2ZrPh_2$ catalyst was stored in an amber vial at −30° C. $^1H$ NMR ($d_6$-benzene): δ 7.35 (d, 4H), 7.20 (t, 4H), 7.12 (q, 2H), 5.77 (s, 10H). Elemental analysis, Calc: C, 70.33%; H, 5.37%; Zr, 24.30%. Anal: C, 68.83%; H, 5.29%; Zr, 23.12.

Example 2

Synthesis of Polyphenylsilane $PhSiH_3$ (22 g, 400 mmol) and $Cp_2ZrPh_2$ (0.381 g, 2 mmol) were mixed together in a Schlenk flask in the glove box. The reaction started immediately after mixing with the observation of $H_2$ gas evolution. The flask was then connected to Schlenk line within 10 min. The reaction mixture was stirred under argon flow for 5 days at room temperature. To remove the Zr catalyst, the yellow to brown polyphenylsilane as synthesized was dissolved in 120 ml toluene, washed 5 times with 3% HCl (150 ml acidic water, stirred for 20 min. in each wash) and once with 150 ml DI water (stirring for 20 min). The polyphenylsilane solution was then purified with chromatography using 60 g Florisil (Aldrich, 100-200 mesh) as the stationary phase and toluene as solvent. About 300 ml eluant was collected into a 500 ml flask. The toluene was removed at room temperature and the polyphenylsilane was further dried under vacuum at 80° C. for two hours to get 19.6 g clear or slightly yellow product (yield: 89%). $^1H$ NMR ($d_6$-benzene): δ 7.2 (bs, 5H), 5.1 (bs, 0.2H), 4.6 (bs, 0.8H).

Figure 5:
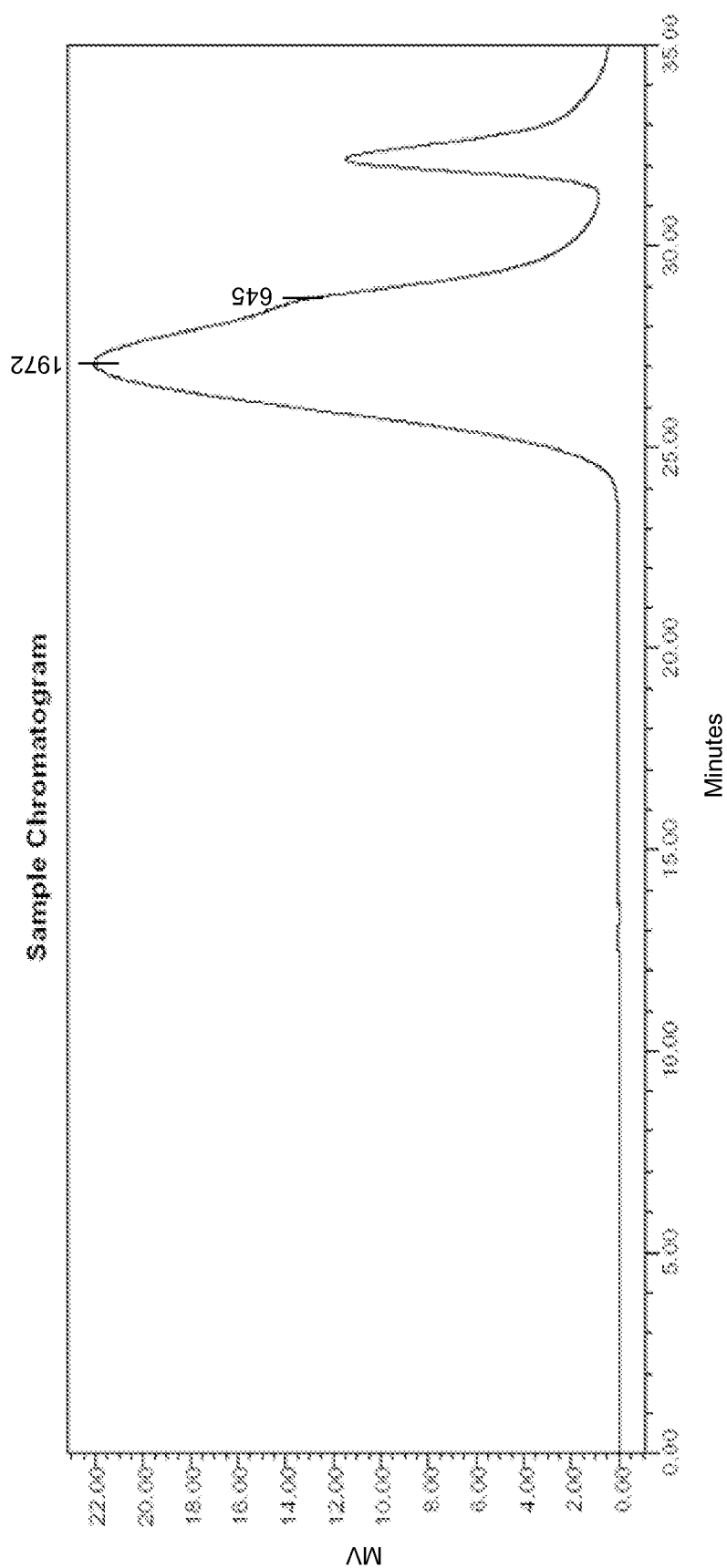
FIG. 5 shows a GPC trace of a typical polyphenylsilane synthesized by an example of the present method.

FIG. 5 shows a GPC trace of a typical polyphenylsilane synthesized by this procedure. The polymer has a bimodal distribution. The lower molecular weight fraction contains a mixture of cyclic silanes with approximately five to six Si units. According to the number average molecular weight Mn as indicated in Table 1 below for the entire product distribution, the polyphenylsilane product mixture contains an average of about 10 to 12 Si units. Thus, the higher molecular weight fraction is believed to contain predominantly the desired linear polyphenylsilane and have an average of more than 10-12 Si units. Thus, n, b and/or q*m may be defined as an average number of silicon and/or germanium atoms in the polysilane (or the dehydrocoupling reaction product mixture), as calculated from the number average molecular weight (Mn) of the polysilane. The cyclic compounds are reasonably unavoidable byproducts, due to the mechanism of the catalyst and the stable nature of the cyclic compounds. The average yield of cyclic compound is about 20% as determined by $^1H$ NMR spectroscopy (the proton chemical shift of cyclic silane is around 5.1 ppm, and the linear polymer is around 4.6 ppm; see, e.g., FIG. 6A). Thus, the higher molecular weight fraction is believed to have an average of about 11 to 14 Si units.

TABLE 1

Molecular weight variation of linear polyphenylsilanes.

| Batch | Mw | Mn | Linear %* |
|---|---|---|---|
| 1 | 2370 | 1340 | 83 |
| 2 | 2280 | 1260 | 79 |
| 3 | 2880 | 1450 | 81 |
| 4 | 2094 | 1161 | 79 |
| 5 | 2310 | 1240 | 82 |

Mw: weight avg. molecular weight;
Mn: number avg. molecular weight;
*:estimated from NMR spectra.

The above described polyphenylsilane purification procedure advantageously removes substantially all of the Zr catalyst. As shown in Table 2 below, the Zr content is about 0.23% if the polyphenylsilane is only washed with water. The amount is reduced to below 0.00001% with the combination of water washing and chromatography. Such reductions advantageously improve stability of a subsequently-produced polysilane.

The stability of polysilane was tested by exposing a 15% polysilane ink in cyclooctane under light at 50° C. A higher Zr content in the polyphenylsilane results in less stable polysilane inks. By removing substantially all of the Zr in the polyphenylsilane, the polysilane ink can survive more than 20 days at 50° C. in light. An ink of polysilanes synthesized from polyphenylsilane with a higher Zr content usually forms a white precipitate within three days under the same conditions.

TABLE 2

Stability of polysilanes.

| Batch | Polyphenylsilane workup | Zr % in polyphenylsilane | Stability of polysilane, days |
|---|---|---|---|
| 1 | Water wash only | 0.23 | 3 |
| 2 | Water wash + chromatography | <0.00001 | >20 |
| 3 | Water wash + chromatography | 0.00005 | >20 |
| 4 | Water wash + chromatography | <0.00001 | >20 |
| 5 | Water wash + chromatography | <0.00001 | >20 |

Example 3

Synthesis of Polysilane

In a 500 ml Schlenk flask, 9 g of polyphenylsilane obtained as above described was dissolved with 100 ml of purified cyclohexane, and 0.25 g sublimed $AlCl_3$ was added to the solution. The flask was connected to a Schlenk line. The reaction mixture was frozen in liquid nitrogen and left under vacuum. The reaction mixture was thawed with a water bath while under static vacuum. Dry HCl gas was then backfilled into the reaction flask under vigorous stirring at room temperature. The solution was stirred 3 hours under continuous HCl flow. After stopping the HCl flow, the solution was stirred overnight under a static HCl atmosphere. The reaction solution was then connected to vacuum for about a minute to remove excess HCl.

36 ml 1M LAH solution (purified as described above) was added to the resulting polychlorosilane solution at 0 to −10° C. The addition was finished in about 30 min, and the reaction mixture was brought to room temperature and stirred overnight. Two phases were formed during this period. The top clear phase containing polysilane was decanted into another Schlenk flask, and was concentrated to about 10 ml by vacuum. The resulting polysilane cyclohexane solution was transferred to an amber vial containing 20 ml degassed DI water. The two phases were mixed vigorously, and allowed to set for 1 min. The top phase containing polysilane was transferred to another vial, and the same water wash procedure was repeated. After the second water wash, the polysilane phase was filtered through a 0.2 μm membrane to obtain a clear liquid which was dried under vacuum for 2 hours. 1.2 g of the final product was obtained as a slightly viscous clear liquid (yield 45%). $^1H$ NMR ($d_6$-benzene): δ 3.5 (bs, SiH) (see, e.g., FIG. 6C). $^{29}Si$ NMR ($d_6$-benzene): δ −96 ($SiH_3$), −106 ($SiH_2$), −128 (SiH).

Treating the polysilane mixture with water after reduction reduces the amount of Al in the polysilane, and substantially removes Al contamination in the Si film after spin coating. The treatment with water may also be carried out with slightly acidic water. Exposure of the silane mixture to alkaline conditions should be avoided as it may lead to uncontrolled Si—Si bond scission and polymerization. Contact with water can occur by either adding the polysilane mixture to water or adding the water to the polysilane mixture. The ratio of water to polysilane mixture is about 2:1. In most cases, washing the polysilane once is enough to remove most Al contamination. However, the reaction of Al residue with water may vary due to the nature of long chain polymer. Washing the polysilane at least twice with water ensures a consistent Al removal effect.

Figure 6:
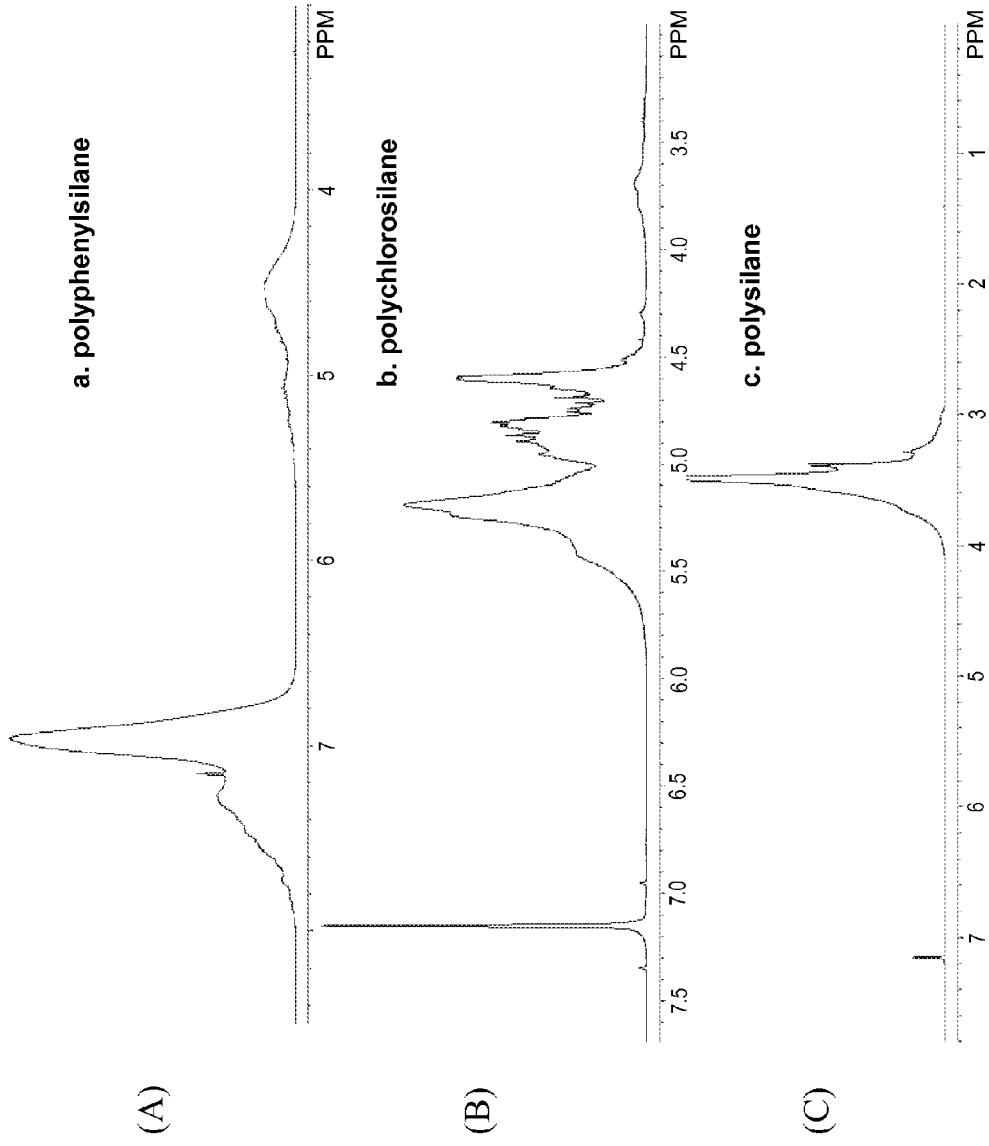
FIGS. 6(A)-(C) show $^1H$ NMR spectra of an isolated polyphenylsilane (FIG. 6a), polychlorosilane (FIG. 6b), and polysilane (FIG. 6c), synthesized by examples of the present method.

The polychlorosilane and polysilane are generally light and temperature sensitive. The $^1H$ NMR spectrum of an isolated polychlorosilane is shown in FIG. 6B. To avoid any unwanted isomerization or generation of higher molecular weight components, the reaction setup is preferable protected from light and UV, for example, using amber flask or wrapping with aluminum foil. The isolated neat polysilane is stored in amber vial at low temperature (−30° C.).

Example 5

In separate procedures, $PhSiH_3$ was dehydrocoupled using $Cp_2ZrPh_2$ and $Cp_2ZrBu_2$ catalysts (generated in situ by reacting $Cp_2ZrCl_2$ with, e.g., 2 mole equivalents of PhMgBr and BuLi, respectively) to yield a polyphenylsilane. The catalyst in the resulting polyphenylsilane was removed as described above. Cleavage of the phenyl groups and reduction of the product as described above yielded a polyhydrosilane, which was used in a viscous ink (e.g., about 10 wt. % in cyclooctane) for spincoating (with and without UV irradiation) and inkjet printing of silicon films.

Example 6

As shown in FIG. 3, cyclo-$Si_5H_6$ was dehydrocoupled using $(Fl_2SiMe_2)ZrBu_2$ catalyst (where Fl is fluorenyl), and the metal catalyst was removed by above described method to yield an oligohydrosilane, which was used in an ink (e.g., about 10 wt. % in cyclooctane) for UV-spincoating and inkjet printing of silicon films. The thus-produced oligohydrosilane exhibited beneficial effects in increasing the ink viscosity relative to similar compositions that did not include such an oligohydrosilane.

Example 7

Si Film Formation

Figure 7:
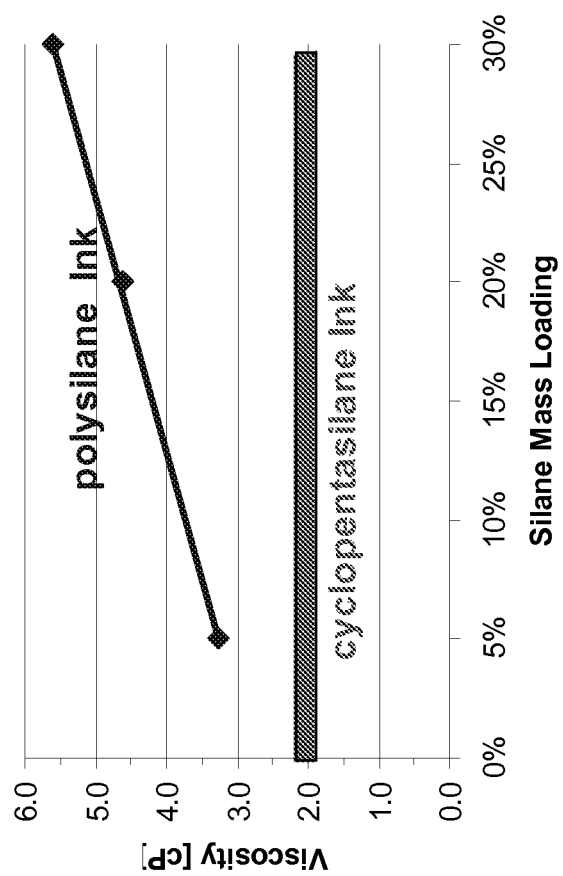
FIG. 7 is a graph showing the viscosity of exemplary polysilane inks as a function of the polysilane mass loading in the ink.

The silane ink is formed by dissolving the polysilane in a compatible organic solvent, such as a mono- or multicyclic aliphatic hydrocarbon (e.g., cyclooctane and/or cis-decalin). The goal is to form a silane film or island from a polysilane ink by an ink jet printing technique. For effective ink jet printing, the ink should have a viscosity >3 cP (preferably about 10 cP) and low volatility. Inks from the present polysilanes meet these specifications. As shown in FIG. 7, the viscosity of the polysilane ink is above 4 cP when the mass loading is above 15% (either wt. % or vol. %), while the viscosity of a similar cyclopentasilane ink is just around 2 cp.

Figure 8:
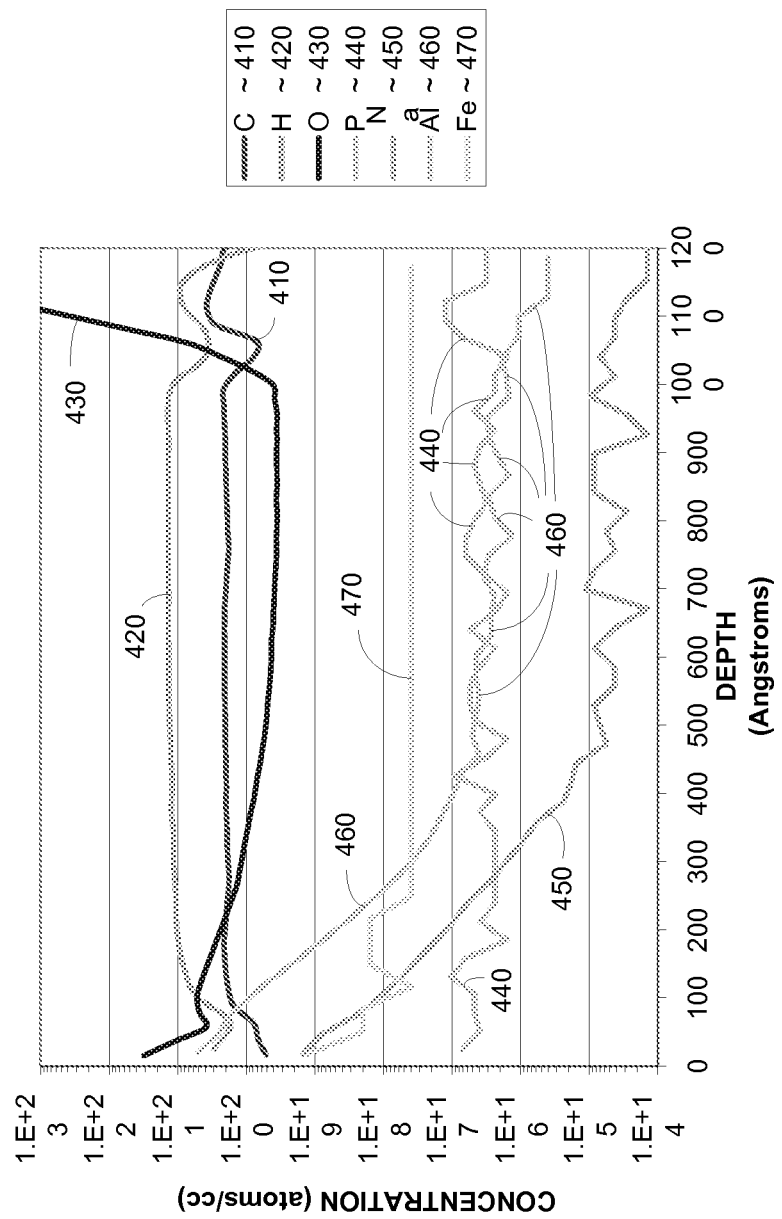
FIG. 8 is a typical SIMS profile of certain impurity atoms in an exemplary silicon film made by an example of the present invention.

A silane film was formed by a spin-coating technique. About 0.4 ml of an ink containing ~10 vol % polysilane in cyclooctane was dispensed onto a substrate in the glove box. A silane film was formed by spin-coating the ink onto the substrate with substantially simultaneous UV irradiation. The substrate with the silane film formed thereon was soft cured on a hotplate at 100° C. for about 10 min, then hard cured in a 400° C. oven under argon flow for 20 min. This procedure formed a hydrogenated, amorphous silicon film with a thickness of from 50 to 100 nm, depending on the spin-coating conditions and ink concentration. A typical SIMS profile of certain impurity atoms in the obtained film is shown in FIG. 8. The carbon, oxygen, hydrogen content in the film is about 0.08%, 0.03%, and 2.8%, respectively. Al is present in an amount of about 0.06 ppm. Both Fe and Na content are below the SIMS detection limit.

CONCLUSION/SUMMARY

As described above, poly- and oligo-hydrosilane and -hydrogermane compounds for semiconductor inks can be synthesized by dehydrocoupling of perhydrosilanes and perhydrogermanes (linear, branched, cyclo-, caged, poly-, or oligosilanes and/or -germanes), or by dehydrocoupling of arylhydrosilanes and arylhydrogermanes, followed by halogenative cleavage of the aryl groups and reduction to yield perhydrosilanes and perhydrogermanes. The inks can be used for production of amorphous and polycrystalline silicon, germanium, or silicon-germanium films by spincoating or inkjet printing, followed by curing at 400-500° C. and (optionally) laser-, heat-, or metal-induced crystallization (and/or dopant activation, when dopant is present; also see, e.g., U.S. application Ser. No. 11/249,167, filed Oct. 11, 2005, and incorporated herein by reference in its entirety). Highly doped films may be used to make contact layers in MOS capacitors, TFTs, diodes, etc. Lightly doped films may be used as semiconductor films in MOS capacitors, TFTs, diodes, etc.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method of making a polyhalosilane, polyhalogermane, or polyhalosilagermane, comprising reacting a polyarylsilane, polyarylgermane, or polyarylsilagermane containing a linear, branched, cyclic or caged chain of at least 15 silicon and/or germanium atoms having substituents bound thereto selected from the group consisting of aryl, substituted aryl and hydrogen, said substituents including a plurality of aryl and/or substituted aryl groups, with (i) a halogen source and (optionally) a Lewis acid or (ii) trifluoromethane-sulfonic acid (HOTf) to form said polyhalosilane, polyhalogermane, or polyhalosilagermane.

2. The method of claim 1, wherein said polyarylsilane, polyarylgermane, or polyarylsilagermane includes a linear, branched, cyclic or caged chain of at least 15 silicon atoms.

3. The method of claim 2, wherein said polyarylsilane further includes at least one aryl and/or substituted aryl group covalently bound to each silicon atom.

4. The method of claim 3, wherein said aryl and/or substituted aryl group is phenyl.

5. The method of claim 1, comprising reacting said polyarylsilane, polyarylgermane, or polyarylsilagermane with said halogen source.

6. The method of claim 5, further comprising reacting said polyarylsilane, polyarylgermane, or polyarylsilagermane and said halogen source with said Lewis acid, wherein said halogen source comprises HCl, and said Lewis acid comprises $AlCl_3$.

7. The method of claim 5, wherein said halogen source comprises HBr or HOTf.

8. The method of claim 1, further comprising reducing said polyhalosilane, polyhalogermane, or polyhalosilagermane with a metal hydride to form a polysilane, polygermane, or polysilagermane consisting essentially of (i) a linear, branched, cyclic or caged chain of at least 15 silicon and/or germanium atoms and (ii) hydrogen atoms.

9. The method of claim 8, wherein said metal hydride comprises a compound of the formula $M^1_a M^2_b H_c R^6_d$, where $M^1$ and $M^2$ are independently first and second metals, each $R^6$ in said metal hydride compound is independently a ligand bound to at least one of $M^1$ and $M^2$ by a covalent, ionic or coordination bond, at least one of a and b is at least 1, c is at least 1, and d is 0 or any integer up to one less than the number of ligand binding sites available on the (a+b) instances of $M^1$ and $M^2$.

10. The method of claim 9, wherein $M^1$ is Li, Na or Ca, $M^2$ is B or Al, each $R^6$ is H, a and b are each at least 1, c is 1, and d is one less than the number of ligand binding sites available on the (a+b) instances of $M^1$ and $M^2$.

11. The method of claim 1, further comprising preparing said polyarylsilane, polyarylgermane, or polyarylsilagermane by a process comprising combining (i) a silane or germane of the formula $AH_a R^1_{4-a}$, (ii) a silane, germane, or silagermane compound of the formula $A_k H_g R^1_h$, or (iii) a combination thereof, where each instance of A is independently Si or Ge, a=2 or 3, and each instance of $R^1$ is independently aryl, substituted aryl, or $-A_b H_{b+1} R^2_b$ (where $R^2$ is aryl or substituted aryl); k is an integer from 2 to 12, $g \geq 2$, h=2 or k, and (g+h)=2k+2; and a metallocene catalyst of early transition metal to form said polyarylsilane.

12. The method of claim 11, wherein said metallocene catalyst has the formula $R^4_2 R^5_2 M$ (or an immobilized derivative thereof), where M is an selected from the group consisting of Ti, Zr and Hf, each of the instances of $R^4$ is independently a substituted or non-substituted cyclopentadienyl, indenyl, or fluorenyl ligand; and each of the instances of $R^5$ is independently a substituted or non-substituted aryl.

13. The method of claim 11, wherein $R^1$ and $R^2$ are each phenyl.

14. A method of making a polysilane, polygermane, or polysilagermane, comprising:
a) reacting a polyhalosilane, polyhalogermane, or polyhalosilagermane containing a linear, branched, cyclic or caged chain of at least 15 silicon and/or germanium atoms having halogen substituents bound thereto with a metal hydride to form the polysilane, polygermane, or polysilagermane; and
b) isolating the polysilane, polygermane, or polysilagermane.

15. The method of claim 14, wherein said polyhalosilane, polyhalogermane, or polyhalosilagermane includes a linear, branched, cyclic or caged chain of at least 15 silicon atoms.

16. The method of claim 15, wherein said polyhalosilane further includes at least one halogen atom covalently bound to each silicon atom.

17. The method of claim 16, wherein said polyhalosilane consists essentially of (i) said linear, branched, cyclic or caged chain of at least 15 silicon atoms, and (ii) halogen atoms.

18. The method of claim 17, wherein said halogen atoms are selected from the group consisting of Cl and Br.

19. The method of claim 14, wherein said metal hydride comprises a compound of the formula $M^1_aM^2_bH_cR^6_d$, where $M^1$ and $M^2$ are independently first and second metals, each $R^6$ in said metal hydride compound is independently a ligand bound to at least one of $M^1$ and $M^2$ by a covalent, ionic or coordination bond, at least one of a and b is at least 1, c is at least 1, and d is 0 or any integer up to one less than the number of ligand binding sites available on the (a+b) instances of $M^1$ and $M^2$.

20. The method of claim 16, wherein $M^1$ is Li, Na or Ca, $M^2$ is B or Al, each $R^6$ is H, a and b are each at least 1, c is 1, and d is one less than the number of ligand binding sites available on the (a+b) instances of $M^1$ and $M^2$.

21. The method of claim 19, wherein said metal hydride is selected from the group consisting of lithium aluminum hydride, calcium aluminum hydride, sodium borohydride, aluminum hydride, gallium hydride, and aluminum borohydride.

22. The method of claim 14, wherein said polysilane, polygermane, or polysilagermane consists essentially of (i) a linear, branched, cyclic or caged chain of at least 15 silicon atoms and (ii) hydrogen atoms.

23. The method of claim 14, further comprising preparing said polyhalosilane, polyhalogermane, or polyhalosilagermane by a process comprising reacting a polyarylsilane, polyarylogermane, or polyarylsilagermane containing a linear, branched, cyclic or caged chain of at least 15 silicon and/or germanium atoms having substituents bound thereto selected from the group consisting of aryl, substituted aryl and hydrogen, said substituents including a plurality of aryl and/or substituted aryl groups, with (i) a halogen source and (optionally) a Lewis acid or (ii) trifluoromethanesulfonic acid (HOTf) to form said polyhalosilane, polyhalogermane, or polyhalosilagermane.

24. The method of claim 14, wherein said halogen substituents are Cl.

* * * * *